United States Patent [19]
Capon et al.

[11] Patent Number: 6,103,521
[45] Date of Patent: Aug. 15, 2000

[54] MULTISPECIFIC CHIMERIC RECEPTORS

[75] Inventors: Daniel J. Capon, Hillsborough; Douglas H. Smith, Foster City; Huan Tian, Cupertino; Genine A. Winslow, Hayward, all of Calif.; Miriam Siekevitz, New York, N.Y.

[73] Assignee: Cell Genesys, Inc., Foster City, Calif.

[21] Appl. No.: 08/454,098

[22] Filed: May 30, 1995

Related U.S. Application Data

[63] Continuation of application No. 08/384,033, Feb. 6, 1995, abandoned.

[51] Int. Cl.$^7$ .......................... C12N 15/62; C07K 14/705
[52] U.S. Cl. .................... 435/325; 435/69.7; 435/320.1; 530/350; 530/387.3; 536/23.4
[58] Field of Search .......................... 536/23.4; 435/69.1, 435/240.2, 252.3, 320.1, 325, 69.7; 530/350, 351, 387.1, 387.3

[56] References Cited

U.S. PATENT DOCUMENTS

| | | | |
|---|---|---|---|
| 5,260,203 | 11/1993 | Ladner et al. | 435/172.3 |
| 5,336,603 | 8/1994 | Capon et al. | 435/69.7 |
| 5,359,046 | 10/1994 | Capon et al. | 536/23.4 |
| 5,741,899 | 4/1998 | Capon et al. | 536/23.4 |

FOREIGN PATENT DOCUMENTS

| | | |
|---|---|---|
| 0340793 | 5/1988 | European Pat. Off. |
| 0610046 | 8/1994 | European Pat. Off. |
| WO 88/09344 | 12/1988 | WIPO |
| WO 91/04329 | 4/1991 | WIPO |
| 9210591 | 6/1992 | WIPO |
| 9215322 | 9/1992 | WIPO |
| WO 93/02198 | 2/1993 | WIPO |
| WO 93/11161 | 6/1993 | WIPO |
| WO9319163 | 9/1993 | WIPO |
| WO 94/04691 | 3/1994 | WIPO |
| WO 94/12520 | 6/1994 | WIPO |
| WO 94/13806 | 6/1994 | WIPO |
| WO 94/22914 | 10/1994 | WIPO |
| 9502686 | 1/1995 | WIPO |

OTHER PUBLICATIONS

Bird et al., J.Biol.Chem. 265:19151–19157, (1990).
Caruso, Mol.Med.Today 2:181–223, (1996).
Coghlan, New Scientist, Nov., (1995).
Culver et al., TIG 10:174–178, (1994).
Stein et al., Cell Biol. 14:3392–3402, (1994).
Gorny et al., J.Virol. 66:7538–7542, (1992).
Gorochov et al., Int.J.Cancer 7:53–57, (1992).
Gross et al., Proc.Natl.Acad.Sci. 86:10024–10028, (1989).
Gunzburg et al., Mol.Med.Today pp. 410–417, (1995).
Heinzel et al., J.Virol. 62:3738–3746, (1988).
Olshevsky et al., J.Virol. 64:5701–5707, (1990).
Hoffman–LaRoche, Curr.Opin.Ther.Pat. 12:2049, (1992).
Marshall, Science p. 1751, (1995).
Mastrangelo et al., Seminars in Oncology 23:4–21, (1996).
Sodroski et al., Nature 322:470–474, (1986).
Spencer et al. (1993) 262,1019–1024.

Eshar et al., "Specific activation and targeting of cytotoxic lymphocytes through chimeric single chains consisting of antibody–binding domains and the γ or ζ subunits of the immunoglobulin and T–cell receptors", *Proc. Natl. Acad. Sci., USA*, 90:720–724, (1993).
Kishimoto et al., "Cytokine Signal Transduction", *Cell*, 76:253–262, (1994).
Kolanus et al., "T Cell Activation by Clustered Tyrosine Kinases", *Cell*, 74:171–183, (1993).
Miyazaki et al., "Functional Activation of Jak1 and Jak3 by Selective Association with IL–2 Receptor Subunits", *Science*, 266:1045–1047, (1994).
Roberts et al., "Targeting of Human Immunodeficiency Virus–Infected Cells by CD28$^+$ T Lymphocytes Armed With Universal T–Cell Receptors", *Blood*, 84(9):2878–2889, (1994).
Sato et al., "Multimeric cytokine receptors: common versus specific functions", *Current Opinion in Cell Biology*, 6:174–179, (1994).
Schlessinger et al., "Growth Factor Signaling by Receptor Tyrosine Kinases", *Neuron*, 9:383–391, (1992).
Stahl et al., "The Alphas, Betas, and Kinases of Cytokine Receptor Complexes", *Cell*, 74:587–590, (1993).
Ullrich et al., "Signal Transduction by Receptors with Tyrosine Kinase Activity", *Cell*, 61:203–212, (1990).

(List continued on next page.)

*Primary Examiner*—Anthony C. Caputa
*Assistant Examiner*—Michael Pak
*Attorney, Agent, or Firm*—Sughrue, Mion, Zinn, Macpeak & Seas, PLLC

[57] ABSTRACT

Novel multispecific chimeric receptor DNA sequences, expression cassettes and vectors containing these sequences as well as cells containing the chimeric DNA and novel chimeric receptor proteins expressed from the sequences are provided in the present invention. The novel multispecific chimeric receptor DNA and amino acid sequences comprise at least three domains that do not naturally exist together: (1) a multispecific binding domain comprising at least two extracellular inducer-responsive clustering domains which serves to bind at least one specific inducer molecule, (2) a transmembrane domain, which crosses the plasma membrane, and (3) either a proliferation signaling domain that signals the cell to divide, or an effector function signaling domain which directs a host cell to perform its specialized function. Optionally, all the multispecific chimeric receptors may contain one or more intracellular inducer-responsive clustering domains attached to one or more of the cytoplasmic signaling domains or the transmembrane domain. The present invention also relates to novel hybrid multispecific chimeric receptors comprising at least one proliferation signaling domain and at least one effector function signaling domain together on the multispecific receptor molecule. The present invention further relates to therapeutic methods and strategies that employ the cells expressing these novel chimeric receptors for the treatment of cancer, infectious disease and autoimmune disease which may have greater therapeutic benefit over a combination of drug therapies.

47 Claims, 4 Drawing Sheets

OTHER PUBLICATIONS

Weiss et al., "T Cell Antigen Receptor Signal Transduction: A Tale of Tails and Cytoplasmic Protein–Tyrosine Kinases", *Cell*, 73:209–212, (1993).

Wilks et al., "Two Novel Protein–Tyrosine Kinases, Each with a Second Phosphotransferase–Related Catalytic Domain, Define a New Class of Protein Kinase", *Molecular and Cellular Biology*, 11(4):2057–2065, (1991).

Witthuhn et al., "JAK2 Associates with the Erythropoietin Receptor and Is Tyrosine Phosphorylated and Activated following Stimulation with Erythropoietin", *Cell*, 74:227–236, (1993).

OLIGO 1    CTGCGTCAACACAGACTGTGAGGAGACGGTGACCAG

OLIGO 2    ACAGACTGTGAGGAGA

OLIGO 3    CTGCGTCAACACAGACTGACCCTTACCCTCAGAAGATTTA-
           CCCGACCCCGAGGTCGACCCTGAGGAGACGGTGACCAG

OLIGO 4    AGAAGATTTACCCGAC

OLIGO 5    CTGCGTCAACACAGACTGACCGTCCTTCTTAGCGTCGTCC
           TTCTTAGCGTCGTCCTTCTTAGCAGCGTCCTTCTTAGCGTCGT
           CAGCGGAAGATGAGGAGACGGTGACCAG

OLIGO 6    GCGTCGTCCTTCTTAG

OLIGO 7    CTGCGTCAACACAGACTGTGGGGACGGTGGGGATGTGTG
           AGTTTTGTCTGAGGAGACGGTGACCAG

OLIGO 8    CGGTGGGGATGTGTGA

OLIGO 9    CTGCGTCAACACAGACTGGTCCAGCTCCCCGTCCTGCGCTTC
           GGCGCTCGATTCTTCCAGTTGCAGCTCTGAGGAGACGGTGAC
           CAG

OLIGO 10   TCGGCGCTCGATTCTT

OLIGO 11   GCCCAGCACCACTTTCTTTGAGCTCACGGTGACCGT

OLIGO 12   ACTTTCTTTGAGCTCA

OLIGO 13   GCCCAGCACCACTTTCTTACCCTTACCCTCAGAAGATTTAC
           CCGACCCCGAGGTCGACCCTGAGCTCACGGTGACCGT

OLIGO 14   GCCCAGCACCACTTTCTTACCGTCCTTCTTAGCGTCGTCCTT
           CTTAGCGTCGTCCTTCTTAGCAGCGTCCTTCTTAGCGTCGTCA
           GCGGAAGATGAGCTCACGGTGACCGT

OLIGO 15   GCCCAGCACCACTTTCTTTGGGGACGGTGGGGATGTGTGA
           GTTTTGTCTGAGCTCACGGTGACCGT

FIG. 2A

OLIGO 16   GCCCAGCACCACTTTCTTGTCCAGCTCCCCGTCCTGCGCTTC
           GGCGCTCGATTCTTCCAGTTGCAGCTCTGAGCTCACGGTGAC
           CGT

OLIGO 17   TAGTCTAGGATCTACTGGCTGCAGTTCTTGCTCTCCTCTGTC

OLIGO 18   ACTGGCTGCAGTTCTT

OLIGO 19   AAAACTGTGCGTTACAATTCGTGGGTCCCCTCCTGAGGA

OLIGO 20   TACAATTCGTGGGTCC

OLIGO 21   TCCTATTGTAACAAATGCTTGCCCTGGTCCTCTCTGGAT

OLIGO 22   AAATGCTTGCCCTGGT

FIG. 2B

MULTISPECIFIC CHIMERIC RECEPTORS

This application is a continuation application of application Ser. No. 08/384,033, filed Feb. 5, 1995, which is now abandoned.

TECHNICAL FIELD

The field of the invention relates to the construction and use of novel multispecific chimeric receptors to overcome the obstacles presented by drug-resistance and genetic variation in infectious disease, cancer and autoimmune disease.

BACKGROUND

Agents designed to selectively inhibit the replication of a rapidly growing pathogen or cancer inevitably face a challenge from the development of drug-resistance. This problem is viewed by many clinicians as one of the major impediments to the effective management of malignant disease or the control of infectious agents which undergo major genetic variation. A related dilemma is presented by autoimmune disease, where a disease-causing cell population may be heterogeneous with respect to marker antigens which could be targeted as part of a therapeutic strategy.

The challenge of genetic variation to disease therapy is well illustrated by the problem of antiviral drug-resistance, though a similar situation holds true for resistance to antimicrobials and chemotherapeutics. The clinical emergence of drug-resistant virus has been documented in most instances in which antiviral therapy has been applied, including HIV, herpes simplex virus, varicella zoster virus, cytomegalovirus, influenza A virus, and rhinovirus (Richman, *Curr. Opin. Infect. Dis.* 3:819–823 (1990)). HIV infection provides a clear example of this problem, given its chronic, persistent nature, the high rate of viral replication, and the error-prone character of reverse transcriptase (RT). Resistance has been observed for every HIV antiviral tested, including nucleoside analogs (AZT, ddI, ddC, d4T and TSAO), non-nucleoside RT inhibitors (Merck's L-697,639 and Boehringer Ingelheim's nevirapine), and a protease inhibitor (Richman, *Annu. Rev. Pharmacol. Toxicol.* 32:149–164 (1993)).

The clinical significance of drug-resistance in HIV infection is best documented for AZT. While AZT reduced the rate of mortality in AIDS patients by over half during the first 12 months of treatment, ongoing therapy out to 24 months did not provide any additional advantage to the treated group. The apparent loss of AZT clinical efficacy correlates with the finding that by 12 months of therapy, approximately 90% of individuals with late-stage disease have developed AZT resistant virus (Richman et al., *J. AIDS* 3:743–746 (1990)). Similarly, the loss of antiviral activity observed with the non-nucleoside RT inhibitors within two months of their administration is associated with the rapid appearance of drug-resistant virus (Nunberg et al., *J. Virol.,* 65:4887–4892 (1991); Richman et al., *Proc. Natl. Acad. Sci.,* 88:11241–11245 (1991)).

Thus, while antiviral therapy with single agents can be quite effective for short periods, extended treatment of chronic or latent infections like HIV and the herpes viruses may require the application of combination therapies. Such a strategy is, however, often impractical due to the additional problems of cross-resistance as well as the cumulative side-effects of multiple agents. It is therefore desirable to design an therapeutic agent which can attack the pathogen at multiple points, in a fashion that minimizes cross-resistance, and has the safety profile of a single active agent. The present invention achieves this goal by providing multispecific chimeric receptors.

SUMMARY OF THE INVENTION

The present invention provides novel multispecific chimeric receptors and their applications to human disease therapy. The multispecific chimeric receptors of the present invention are single proteins possessing more than one antigen-binding and/or ligand-binding domain linked to an effector signaling domain and/or a proliferation signaling domain. A principal application of the novel multispecific chimeric receptors of the present invention is to combine the therapeutic benefits of two or more monospecific chimeric effector function receptors in a single protein for the treatment of a disease. In this manner, a multispecific protein product is provided which has the pharmacological profile of a single agent.

DESCRIPTION OF THE DRAWINGS

FIGS. 2A and 2B are listing of oligonucleotides (SEQ ID NOS: 1–22) as described in the Examples, infra.

DETAILED DESCRIPTION OF THE PREFERRED EMBODIMENTS

Figure 1:
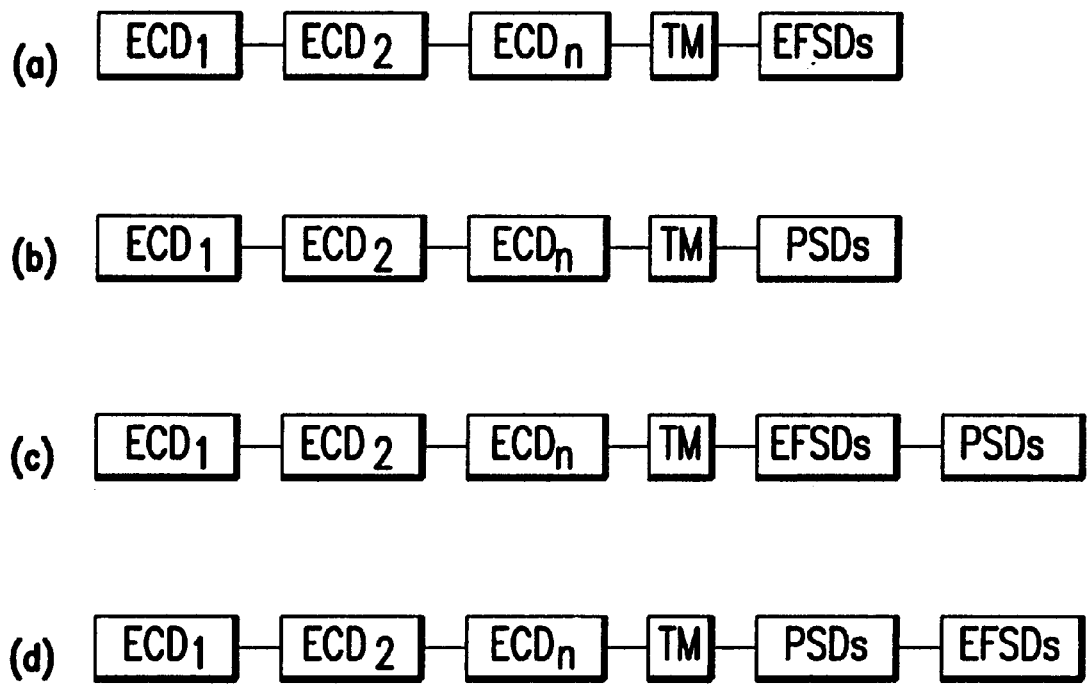
FIG. 1 illustrates the structures of the multispecific chimeric receptors discussed in the detailed description.

As noted above, the present invention generally relates to novel multispecific chimeric receptors, namely, chimeric proliferation receptors, chimeric effector function receptors, and hybrids thereof, each comprising at least two ligand and/or antigen binding domains of different specifities, and DNA sequences encoding these novel chimeric receptors. Further aspects of the present invention will be discussed in detail below following a definition of terms employed herein.

Definitions:

The term "extracellular inducer-responsive clustering domain" or "ECD" refers to the portion of a protein of the present invention which is outside of the plasma membrane of a cell and binds to at least one extracellular inducer molecule as defined below. The ECD may include the entire extracytoplasmic portion of a transmembrane protein, a cell surface or membrane associated protein, a secreted protein, a cell surface targeting protein, a cell adhesion molecule, or a normally intracytoplasmic inducer-binding domain, and truncated or modified portions thereof. In addition, after binding one or more extracellular inducer molecule(s) defined below, the ECDs will become associated with each other by dimerization or oligomerization, i.e., "cluster".

The term "multispecific extracellular inducer-responsive clustering domain" or "MSECD" refers to more than one ECD, as defined above, linked in tandem, either covalently or non-covalently, on the same protein.

The term "intracellular inducer-responsive clustering domain" or "ICD" refers to the portion of a protein which is inside of the plasma membrane of a cell, that binds to at least one intracellular inducer molecule as defined below. After binding one or more intracellular inducer molecule(s), the ICDs will become associated with each other by dimerization or oligomerization, i.e., "cluster".

The term "transmembrane domain" or "TM" refers to the domain of the protein which crosses the plasma membrane and is derived from the inducer-binding ECD domain, the effector function signaling domain, the proliferation signaling domain or a domain associated with a totally different protein. Alternatively, the transmembrane domain may be an artificial hydrophobic amino acid sequence which spans the plasma cell membrane.

The term "proliferation signaling domain" or "PSD" refers to a protein domain which signals the cell to enter mitosis and begin cell growth. Examples include the human or mouse Janus kinases, including but not limited to, JAK1, JAK2, JAK3, Tyk2, Ptk-2, homologous members of the Janus kinase family from other mammalian or eukaryotic species, the IL-2 Receptor β and/or γ chains and other subunits from the cytokine receptor superfamily of proteins that may interact with the Janus kinase family of proteins to transduce a signal, and the cytoplasmic domains from the members of the superfamily of tyrosine kinase growth factor receptors, or portions, modifications or combinations thereof.

The term "effector function" refers to the specialized function of a differentiated cell. Effector function of a T cell, for example, may be cytolytic activity or helper activity including the secretion of cytokines.

The term "effector function signaling domain" or "EFSD" refers to the portion of a protein which transduces the effector function signal and directs the cell to perform its specialized function. While usually the entire EFSD will be employed, in many cases it will not be necessary to use the entire chain. To the extent that a truncated portion of the EFSD may find use, such truncated portion may be used in place of the intact chain as long as it still transduces the effector function signal. Examples are the ζ chain of the T cell receptor or any of its homologs (e.g., η chain, FcεR1-γ and -β chains, MB1 (Igα) chain, B29 (Igβ) chain, etc.), CD3 polypeptides (Δ, δ and ε), syk family tyrosine kinases (Syk, ZAP 70, etc.), src family tyrosine kinases (Lck, Fyn, Lyn, etc.) and other molecules involved in T cell transduction, such as CD2, CD5 and CD28.

The term "linker" or "linker region" refers to an oligo- or polypeptide region of from about 1 to 100 amino acids that links together any of the above described domains of the MSCRs defined above. The amino acid sequence is typically derived from a protein other than the ICDs, ECDs, EFSDs, PSDs or TM domains. Examples of linker regions are linker 212 and linker 205 as referenced in Bedzyk et al., *J. Biol. Chem.*, 265:18615–18620 (1990) and Gruber et al., *J. Immunol.*, 152:5368–5374 (1994), respectively.

The term "membrane hinge" refers to a hydrophilic polypeptide sequence found in membrane-bound immunoglobulin heavy chains, where it is attached to the extracellular side of the TM domain (Bensmana & Lefranc, *Immunogenetics*, 32:321–330 (1990)). As used in the present invention, the membrane hinge may be considered a subset of linkers.

The term "chimeric inducer-responsive proliferation receptor" or "CPR" refers to a chimeric receptor that comprises an extracellular inducer responsive clustering domain (ECD), a transmembrane domain (TM) and at least one proliferation signaling domain (PSD). The ECD and PSD are not naturally found together on a single protein receptor. Optionally, this chimeric receptor may also contain an effector function signaling domain to form a "hybrid MSCR" as defined below.

The term "chimeric effector function receptor" or "CEFR" refers to a chimeric receptor that comprises an extracellular domain, transmembrane domain, and at least one cytoplasmic domain as described in U.S. Pat. No. 5,359,046 or at least one EFSD domain as described above. The extracellular domain serves to bind to an extracellular inducer and transmit a signal to the cytoplasmic domain which transduces an effector function signal to the cell.

The term "multispecific chimeric effector function receptor" or "MSCEFR" refers to a chimeric effector function receptor which contains a multispecific extracellular inducer-responsive clustering domain (MSECD).

The term "multispecific chimeric proliferation receptor" or "MSCPR" refers to a chimeric inducer-responsive proliferation receptor which contains a multispecific extracellular inducer-responsive clustering domain (MSECD).

The term "hybrid MSCR" refers to a chimeric receptor that comprises a MSECD, a TM and at least one EFSD and at least one PSD linked together, in either order, directly or via a linker region to the transmembrane domain in either order.

The term "multispecific chimeric receptor" or "MSCR" refers to a chimeric receptor that comprises a multispecific ECD (MSECD), a transmembrane domain (TM) and at least one effector function signaling domain (EFSD) and/or at least one proliferation signaling domain (PSD (i.e. MSCEFRS, MSCPRs and hybrid MSCRs)). In addition, the MSCEFRS, MSCPRs and hybrid MSCRs of the present invention may also have one or more ICDs attached to one or more of their cytoplasmic domains.

The term "extracellular inducer molecule" refers to a ligand or antigen which binds to an ECD and induces the clustering of the ECD or MSECD as described above, or portions or modifications of the extracellular inducer molecule that are still capable of binding to the ECD and inducing the clustering of an MSECD. To facilitate clustering, the extracellular inducer molecule may be intrinsically bivalent or multivalent; or it may be presented to the ECD in a bivalent or multivalent form, eg., on the surface of a cell or a virus.

The term "intracellular inducer molecule" refers to a natural or synthetic ligand that can be delivered to the cytoplasm of a cell, and binds to and induces the clustering of an intracellular-inducer responsive domain (ICD). To facilitate clustering, the intracellular inducer molecule may be intrinsically bivalent or multivalent.

The term "multispecific antibody" refers to an antibody molecule, or truncations or modifications thereof, that comprises two or more ECDs of different specificities.

The term "modifications" refers to an addition of one or more amino acids to either or both of the C- and N-terminal ends of the extracellular or intracellular inducer molecules (in the case where these are proteins) or, the ECDs, PSDs, EFSDS, ICDs or TMs, a substitution of one or more amino acids at one or more sites throughout these proteins, a deletion of one or more amino acids within or at either or both ends of these proteins, or an insertion of one or more amino acids at one or more sites in these proteins such that the extracellular or intracellular inducer molecule binding to the ECD or ICD is retained or improved as measured by binding assays known in the art, for example, Scatchard plots, or such that the PSD, EFSD, ICD or TM domain activities are retained or improved as measured by one or more of the proliferation assays or effector assays described below. In addition, modifications can be made to the extracellular or intracellular inducer molecules (where they are proteins) and to the corresponding ECDs or ICDs to create an improved receptor-ligand binding pair.

The term "variant" refers to a DNA fragment encoding an extracellular or intracellular inducer molecule, or an ECD, PSD, EFSD, ICD or TM domain that may further contain an addition of one or more nucleotides internally or at the 5' or 3' end of the DNA fragment, a deletion of one or more nucleotides internally or at the 5' or 3' end of the DNA fragment or a substitution of one or more nucleotides internallly or at the 5' or 3' end of the DNA fragment such that the extracellular or intracellular inducer molecule binding to the ECD or ICD is retained or improved as measured by binding assays known in the art, for example, Scatchard plots, or such that the PSD, EFSD, ICD or TM domain activities are retained or improved as measured by one or more of the proliferation assays or effector assays described below. In addition, variants of the DNA sequences encoding the extracellular and intracellular inducer molecules (where they are proteins) and the corresponding ECDs and ICDs can be made so as to create an improved receptor-ligand binding pair.

In a general embodiment, the present invention relates to novel multispecific chimeric receptors, nucleic acid sequences encoding the receptors, the vectors containing the nucleic acids encoding the receptors, the host cells expressing these novel multispecific chimeric receptors, and methods of using these novel multispecific chimeric receptors as therapeutics. Three types of multispecific chimeric receptors (MSCR) are provided herein, namely, multispecific chimeric proliferation receptors (MSCPR) (FIG. 1(b)), multispecific chimeric effector function receptors (MSCEFR) (FIG. 1(a)) and hybrid MSCRs comprising both an effector signaling domain and a proliferation signaling domain (FIGS. 1(c) and 1(d)). In each category of receptors, the multispecific binding domain, the effector function signaling domain, and the proliferation signaling domain do not naturally exist together on a single protein.

In one particular embodiment, the present invention relates to a multispecific chimeric proliferation receptor (MSCPR) designed to be expressed in cells, which in turn proliferate in response to at least one specific extracellular inducer molecule. The three domains which comprise a MSCPR are: (1) a multispecific binding domain comprising at least two extracellular inducer-responsive clustering domains (ECDs) which serves to bind to at least one specific extracellular molecule, (2) a transmembrane domain, which crosses the plasma membrane and, (3) at least one proliferation signaling domain that signals the cell to divide (FIG. 1(b)).

The cells bearing the MSCPRs of the present invention will expand in number in response to the binding of one or more different specific extracellular molecules to an extracellular inducer-responsive clustering domain of the MSCPR. In each instance, the extracellular inducer molecule binds to at least one ECD, which results in the dimerization or oligomerization of the MSECDs to each other. The clustering of these MSECDs signals activation of the proliferation domain(s).

In another embodiment, the present invention relates to a novel multispecific chimeric effector function receptor (MSCEFR) designed to be expressed in cells, which when activated by the binding of at least one specific extracellular inducer molecule, will induce a specialized effector function of a differentiated cell. The three domains that comprise a MSCEFR are: (1) a multispecific binding domain comprising at least two extracellular inducer-responsive clustering domains (ECDs) which serves to bind to at least one specific extracellular inducer molecule, (2) a transmembrane domain, which crosses the plasma membrane and, (3) at least one effector function signaling domain which tranduces the effector function signal and directs the cell to perform its specialized function (FIG. 1(a)).

The cells bearing the MSCEFRs of the present invention will express effector function in response to the binding of one or more different specific extracellular inducer molecules to an extracellular inducer-responsive clustering domain of the MSCEFR. In each instance, the extracellular inducer molecule binds to at least one ECD, which results in the dimerization or oligomerization of the MSECDs to each other. The clustering of these MSECDs signals activation of the effector function signaling domain(s).

In yet another embodiment, the present invention relates to a novel hybrid multispecific chimeric receptor (hybrid MSCR) containing a proliferation signaling domain and an effector function signaling domain together on the same multispecific receptor. In this particular embodiment, the hybrid receptor comprises a MSECD and TM described above, and additionally comprises at least one effector function signaling domain and at least one proliferation signaling domain joined together on the same protein (FIGS. 1(c) and 1(d)). Thus, the multispecific extracellular inducer responsive clustering domains (MSECDs) of the hybrid MSCR are linked via a transmembrane domain to two different types of signal transducing domains. Either the proliferation signaling domain or the effector function signaling domain may be linked to the transmembrane domain which is further linked on its 3' end to the second signaling domain either directly or through a linker region. It is contemplated that the preparation of this novel hybrid MSCR will activate proliferation and effector function simultaneously in a host cell upon the binding of at least one extracellular inducer molecule to one or more the ECDs of the hybrid MSCR of the present invention.

In yet another aspect of the present invention, a novel multispecific chimeric proliferation receptor containing a multispecific extracellular inducer-responsive clustering domain (MSECD), and a proliferation signaling domain (PSD) is provided together in the same receptor protein with an intracellular inducer-responsive clustering domain (ICD). In this embodiment, a receptor is constructed as one protein comprising in the N-terminal to C-terminal direction a multispecific ECD, TM domain, an ICD and a PSD. Alternatively, a receptor may be constructed as one protein comprising in the N-terminal to C-terminal direction an MSECD, TM domain, PSD and an ICD. In preparing the multispecific chimeric inducer binding receptors of the present embodiment, one may separate one or more domains of each receptor with a linker or membrane hinge region. Additionally, more than one ICD and PSD may be attached directly or via a linker or membrane hinge region to each other to form multiple ICDs and PSDS. Upon introduction of these novel inducer-binding chimeric proliferation receptors into a host cell, one may modulate proliferation of the cell by either an extracellular inducer, an intracellular inducer or a combination of these two different inducer molecules. The embodiment of this aspect of the invention may be modified even further by attaching an effector function signaling domain (EFSD) at the N-terminal or C-terminal end of the PSD or the ICD. A MSECD and multiple ICDs and/or PSDs may be employed in the construction of these receptors. Upon expression of these novel hybrid multispecific receptors containing both an MSECD and an ICD in a host cell, one may modulate proliferation and effector signaling by adding either an extracellular inducer, an intracellular inducer or a combination of these two different inducer molecules.

The extracellular inducer-responsive clustering domain (ECD) may be obtained from any of the wide variety of extracellular domains of eukaryotic transmembrane proteins, secreted proteins or other proteins associated with ligand binding and/or signal transduction. The ECD may be part of a protein which is monomeric, homodimeric, heterodimeric, or associated with a larger number of proteins in a non-covalent or disulfide-bonded complex. To create the multispecific binding domains of the present invention, two or more individual binding domains are connected to each other on a single protein, either covalently or noncovalently. An oligo- or polypeptide linker region may be used to connect these domains to each other.

In particular, the ECDs may consist of monomeric, dimeric or tetrameric immunoglobulin molecules, or portions or modifications thereof, which are prepared in the following manner.

The full-length IgG heavy chain comprising the VH, CH1, hinge, and the CH2 and CH3 (Fc) Ig domains may be fused to a EFSD, PSD or ICD of an MSCR via the appropriate transmembrane domain. If the VH domain alone is sufficient to confer antigen-specificity (so-called "single-domain antibodies"), homodimer formation of the MSCR is expected to be functionally bivalent with regard to antigen binding sites. If both the VH domain and the VL domain are necessary to generate a fully active antigen-binding site, both the VH-containing MSCR and the full-length IgL chain are introduced into cells to generate an active antigen-binding site. Dimer formation resulting from the intermolecular Fc/hinge disulfide bonds results in the assembly of MSCRs with extracellular domains resembling those of IgG antibodies. Derivatives of these MSCRs include those in which only non-Fc regions of the heavy chain are employed in the fusion. For example, the VH domain (and the CH1 domain) of the heavy chain can be retained in the extracellular domain of the MSCR, but MSCR dimers are not formed. As above, the full-length IgL chain can be introduced into cells to generate an active antigen-binding site.

As indicated, the ECD may consist of an Ig heavy chain which may in turn be covalently associated with Ig light chain by virtue of the presence of the CH1 region, or may become covalently associated with other Ig heavy/light chain complexes by virtue of the presence of hinge, CH2 and CH3 domains. The two heavy/light chain complexes may have different specificities, thus creating a MSCR which binds two distinct antigens. Depending on the function of the antibody, the desired structure and the signal transduction, the entire chain may be used or a truncated chain may be used, where all or a part of the CH1, CH2, or CH3 domains may be removed or all or part of the hinge region may be removed.

Because association of both the heavy and light V domains are required to generate a functional antigen binding site of high affinity, in order to generate an antibody-containing MSCR with the potential to bind antigen, a total of two molecules will typically need to be introduced into the host cell. Therefore, an alternative and preferred strategy is to introduce a single molecule bearing a functional antigen binding site. This avoids the technical difficulties that may attend the introduction and coordinated expression of more than one gene construct into host cells. This "single-chain antibody" (SAb) is created by fusing together the variable domains of the heavy and light chains using an oligo- or polypeptide linker, thereby reconstituting an antigen binding site on a single molecule.

Single-chain antibody variable fragments (SAbFv) in which the C-terminus of one variable domain (VH or VL) is tethered to the N-terminus of the other (VL or VH, respectively), via a oligo- or polypeptide linker, have been developed without significantly disrupting antigen binding or specificity of the binding (Bedzyk e al. (1990) *J. Biol. Chem.*, 265:18615; Chaudhary et al. (1990) *Proc. Natl. Acad. Sci.*, 87:9491). The SAbFvs used in the present invention may be of two types depending on the relative order of the VH and VL domains: VH-l-VL or VL-l-VH (where "1" represents the linker). These SAbFvs lack the constant regions (Fc) present in the heavy and light chains of the native antibody. In another aspect of the present invention, the SAbFv fragment may be fused to all or a portion of the constant domains of the heavy chain, and the resulting ECD is joined to the EFSD, PSD or ICD via an appropriate transmembrane domain that will permit expression in the host cell. The resulting MSCRs differ from the SAbFvs, described above, in that upon binding of antigen they initiate signal transduction via their cytoplasmic domain.

Single-chain derivatives of T cell receptors (SCTCRs) in which the variable regions of the T cell receptor α and β chains are joined together by an appropriate oligo- or polypeptide linker may also be employed as one or more of the ECDs contained within an MSCR.

To aid in the proper folding and efficient expression of the MSCRs, including MSCEFRs, MSCPRs and hybrid MSCRS, the antibody-derived ECDs may be connected at their C-terminal end to one of a number of membrane hinge regions which are a normal part of membrane-bound immunoglobulin molecules. For example, the eighteen amino acids of the IGHG3 M1 exon may be used (Bensmana and Lefranc, *Immunogenet.*, 32:321–330 (1990)). The TM domain is attached to the C-terminal end of the membrane hinge. It is also contemplated that membrane hinge sequences may be used to connect non-antibody derived ECDs to the transmembrane domains to increase CPR expression.

Diabodies may also be used as ECDs in the present invention. Diabodies contain two chimeric immunoglobulin chains, one of which comprises a VH domain connected to a VL domain on the same polypeptide chain (VH-VL). A linker that is too short to allow pairing of the VH and VL domains on this chain with each other is used so that the domains will pair with the complementary VH and VL domains on the other chimeric immunoglobulin chain to create two antigen-binding sites (Holliger et al., *Proc. Natl. Acad. Sci.* 90:6444–6448 (1993)). As described above, one of these chains is linked to the membrane hinge and/or the TM domain, which in turn is linked to the EFSD, PSD and/or ICD. The other chain (not connected covalently to a EFSD, PSD or ICD) will be co-expressed in the same cell to create a MSCR with a diabody ECD which will respond to two different extracellular inducer molecules.

In the present invention, the SCFv fragment or the single domain antibody may be fused to all or a portion of the constant domains of the heavy chain or the light chain before being linked to each other to form the multispecific ECD. The MSECDs used in the present invention may comprise (N- to C-terminal) a SCFv fragment linked to another SCFv domain that in turn is linked to all or part of the constant domains (CH1, hinge, CH2 and CH3).

To aid in the proper folding and efficient expression of the MSCRs of the present invention, the antibody-derived ECDs may be connected at their C-terminal end to one of a number of "membrane hinge regions" which are a normal part of membrane-bound immunoglobulin molecules. The TM domain is attached to the C-terminal end of the membrane hinge. For example, eighteen amino acids from the N-terminal end of the IGHG3 M1 exon may be used (Bensmana and Lefranc, *Immunogenet.*, 32:321–330 (1990)). It is contemplated that membrane hinge sequences may be used to connect non-antibody derived ECDs to the transmembrane domains to increase CPR and CEFR expression. In the present invention, the membrane hinge region may also be employed like other linker regions, eg., be attached on either side of a TM, PSD, or ECD.

Ligand-binding domains from naturally occurring receptors may also be used as ECDs to prepare the MSECDs of the present invention, where the receptors are surface membrane proteins, including cell differentiation antigens such as CD4 and CD8, cytokine or hormone receptors or cell adhesion molecules such as ICAM or LFA-1. The receptor may be responsive to a natural ligand, an antibody or fragment thereof, a synthetic molecule, e.g., drug, or any other agent which is capable of inducing a signal. In addition, either member of a ligand/receptor pair, where one is expressed on a target cell such as a cancer cell, a virally infected cell or an autoimmune disease causing cell, may also be used as an ECD in the present invention. In addition, the receptor-binding domains of soluble ligands or portions thereof could be employed as ECDs in the MSECDs of the present invention. In addition, binding portions of antibodies, cytokines, hormones, or serum proteins can be used. Furthermore, secreted targeting molecules such as IL-14 or the soluble components of the cytokine receptors such as IL-6R, IL-4R, and IL-7R can be used as ECDs (Boulay and Paul *Current Biology* 3: 573–581, 1993).

Where a receptor is a molecular complex of proteins, where only one chain has the major role of binding to the ligand, it will usually be desirable to use solely the extracellular portion of the ligand binding protein. Where the extracellular portion may complex with other extracellular portions of other proteins or form covalent bonding through disulfide linkages, one may also provide for the formation of such dimeric or multimeric extracellular regions. Also, where the entire extracellular region is not required, truncated portions thereof may be employed, where such truncated portion is functional. In particular, when the extracellular region of CD4 is employed, one may use only those sequences required for binding of gp120, the HIV envelope glycoprotein. In the case in which immunoglobulin-derived sequences are used to create a multispecific ECD, one may simply use the antigen binding regions of the antibody molecule and dispense with the constant regions of the molecule (for example, the Fc region consisting of the CH2 and CH3 domains).

To create the multispecific ECDs of the present invention, two or more individual ECDs are connected to each other, either covalently or noncovalently, on a single protein molecule. An oligo- or polypeptide linker, an Fc hinge or membrane hinge region may be used to connect these domains to each other. The MSECDs of the present invention may comprise two or more of the different ECDs described above connected together in different combinations. For example, two or more ECDs containing immunoglobulin sequences, (e.g. SCFvs and/or single-domain antibodies) may be linked to each other. In another example, two or more ECDs from membrane proteins (e.g. cytokine receptors and/or CD antigens) may be linked to each other. In yet another example, a MSECD may consist of a mixture of ligand-binding domains and immunoglobulin-derived domains eg., an ECD from CD4 may be joined to a SCFv.

The proliferation signaling domains (PSDS) that comprise the MSCPRs and hybrid MSCRs of the present invention may be obtained from the cytoplasmic signal-transducing domains of the cytokine/hematopoietin receptor superfamily. The members of this mammalian receptor superfamily can transduce proliferative signals in a wide variety of cell types. The cytoplasmic domains of the signal-transducing subunits may contain conserved motifs that are critical for the transduction of proliferative signals (Bazan, *Current Biology*, 3:603–606 (1993); Boulay and Paul, *Current Biology*, 3:573–581 (1993); Wells, *Current Opinion in Cell Biology*, 6:163–173 (1994); Sato and Miyajima, *Current Opinion in Cell Biology*, 6:174–179 (1994); Stahl and Yancopoulos, *Cell*, 74:587–590 (1993); Minami et al., *Ann. Rev. Immunol.*, 11:245–267 (1993); Kishimoto et al., *Cell*, 76:253–262 (1994)). The signal-transducing components of these cytokine receptors to be used as PSDs in the present invention include, but are not limited to, Interleukin-2 receptor β (IL-2Rβ), IL-2Rγ, IL-3Rβ, IL-4R, IL-5Rα, IL-5Rβ, IL-6R, IL-6R gp130, IL-7R, IL-9R, IL-12R, IL-13R, IL-15R, EPO-R (erythropoietin receptor), G-CSFR (granulocyte colony stimulating factor receptor), GM-CSFRα (granulocyte macrophage colony stimulating factor receptor α), GM-CSFRβ, LIFRα (leukemia inhibitory factor receptor α), GHR (growth hormone receptor), PRLR (prolactin receptor), CNTFR (ciliary neurotrophic factor receptor), OSMR (oncostatin M receptor) IFNRα/β (interferon α/β receptor), IFNRγ, TFR (tissue factor receptor), and TPOR (thrombopoietin or mpl-ligand receptor)(Minami et al., *J. Immunol.*, 152:5680–5690 (1994); Boulay and Paul, *Current Biology*, 3:573–581 (1993); Wells, *Current Opinion in Cell Biology*, 6:163–173 (1994)).

The proliferation signaling domains (PSDs) that comprise the MSCPRs and hybrid MSCRs of the present invention may be obtained from the signal-transducing domains of the tyrosine kinase growth factor receptor superfamily or from oncogenes or proto-oncogenes which are related to this growth factor family (Schlessinger and Ullrich, *Cell*, 61:203–212 (1990), Ullrich and Schlessinger, *Neuron*, 9:383–391 (1992)). The members of this mammalian receptor superfamily can transduce proliferative signals in a wide variety of cell types. The cytoplasmic domains of the signal-transducing subunits contain tyrosine kinase domains that are critical for the transduction of proliferative signals. The growth factor receptors, proto-oncogenes, and oncogenes to be used as PSDs in the present invention include, but are not limited to epidermal growth factor receptor (EGF-R), HER2/neu, HER3/c-erbB-3, Xmrk, Insulin-R, IGF-1-R (insulin-like growth factor-1 receptor), IRR, PDGF-R-A (platelet-derived growth factor receptor-A), PDGF-R-B (platelet-derived growth factor receptor-B), CSF-1-R (colony-stimulating factor-1 receptor), c-kit, FGF-R (fibroblast growth factor receptor), acidic FGF-R, and basic FGF-R (Ullrich and Schlessinger, *Cell*, 61:203–212 (1990)).

The proliferation signaling domains employed in constructing the MSCPRs and hybrid MSCRs of the present invention may also be obtained from any member of the Janus or JAK eukaryotic family of tyrosine kinases, including Tyk2, JAKI, JAK2, JAK3 and Ptk-2. Members of the Janus kinase family are found in all cell types. They associate with various signal transducing components of the cytokine receptor superfamily discussed above and respond to the binding of extracellular inducer by the phosphorylation of tyrosines on cytoplasmic substrates (Stahl and Yancopoulos, *Cell,* 74:587–590 (1993)). They are thus an integral part of the control of cell proliferation in many different kinds of cells. The members of this family are marked by similar multidomain structures and a high degree of sequence conservation. Unique among tyrosine kinases, the Janus kinase family may have two non-identical tandem kinase-like domains, only one of which may have catalytic activity (Firmbach-Kraft et al., Oncogene, 5:1329–1336 (1990); Wilks et al., *Mol. Cell. Biol.,* 11:2057–2065 (1991); Harpur et al., *Oncogene,* 7:1347–1353 (1992)). The kinase activity of the Janus kinases is usually activated after the binding of ligands to their associated cytokine family receptors and the oligomerization of the receptors (Stahl and Yancopoulos, *Cell,* 74:587–590 (1993)). This activation, in turn, triggers the initiation of intracellular signaling cascades (Witthuhn et al., *Nature,* 370:153–157 (1994); Russell et al., *Science,* 366:1042–1044 (1994); Kawamura et al., *Proc. Natl. Acad. Sci.,* 91:6374–6378 (1994); Miyazaki et al., *Science,* 266:1045–1047 (1994); Johnston et al., *Nature,* 370:151–153 (1994); Asao et al., *FEBS Letters,* 351:201–206 (1994)).

The effector function signaling domains (EFSDs) employed in the MSCEFRs and hybrid MSCRs of the present invention may be derived from a protein which is known to activate various second messenger pathways. One pathway of interest is that involving phosphatidylinositol-specific phospholipase hydrolysis of phosphatidylinositol-4,5-biphosphate, and production of inositol-1,4,5-trisphosphate and diacylglycerol. The calcium mediated pathway, the tyrosine and serine/threonine kinase and phosphatase pathway, the adenylate cyclase, and the guanylate cyclase pathways may also be second messenger pathways. EFSDs of interest include proteins with ARAM motifs (Reth, *Nature,* 338:383–384 (1989); Weiss, *Cell,* 73:209–212 (1993)), for example, the ζ chain of the T-cell receptor, the η chain, which differs from the ζ chain only in its most C-terminal exon as a result of alternative splicing of the ζ mRNA, the γ and β subunit of the FcεR1 receptor, the MB1 (Igα) and B29 (Igβ) chains of the B cell receptor, and the δ, γ, and ε chains of the T-cell receptor (CD3 chains), other proteins homologous to the above protein subunits including synthetic polypeptides with ARAM motifs, and such other cytoplasmic regions which are capable of transmitting a signal as a result of interacting with other proteins capable of binding to an inducer (Romeo et al., *Cell,* 68:889–897 (1992); Weiss, *Cell,* 73:209–212 (1993)). The syk family of tyrosine kinases may also be used as effector function signaling domains in the present invention. The clustering of these domains from Syk and ZAP-70 leads to the activation of T cell cytolytic activity (Kolanus et al., *Cell,* 74:171–183 (1993)). In addition, the src family of tyrosine kinases (Lck, Fyn, Lyn, etc.) (Rudd et al., *Immunology Today,* 15:225–234 (1994)) and molecules such as CD2, CD5 and CD28, which are involved in T cell transduction, may also be used as EFSDs in the present invention. A number of EFSDs or functional fragments or mutants thereof may be employed, generally ranging from about 50 to 1500 amino acids each, where the entire naturally occurring cytoplasmic region may be employed or only an active portion thereof.

The intracellular clustering domain (ICD) can be obtained from the inducer binding domains of a variety of intracellular proteins. For example, eukaryotic steroid receptor molecules can be used as ICDs (e.g. the receptors for estrogen, progesterone, androgens, glucocorticoids, thyroid hormone, vitamin D, retinoic acid, 9-cis retinoic acid and ecdysone). In addition, variants of steroid and other receptors which fail to bind their native inducer, but still bind to an antagonist, can be prepared by one skilled in the art and used to make the CPRs of this invention. For example, a C-terminal deletion mutant of the human progesterone receptor, which fails to bind progesterone, can be clustered by the addition of progesterone antagonists, including RU 486 (Wang et al., *Proc Natl Acad Sci* 91: 8180–8184, 1994). Binding domains from the eukaryotic immunophilin family of molecules may also be used as ICDs. Examples include but are not limited to members of the cyclophilin family: mammalian cyclophilin A, B and C, yeast cyclophilins 1 and 2, Drosophila cyclophilin analogs such as ninaA; and members of the FKPB family: the various mammalian isoforms of FKBP and the FKBP analog from Neurospora (Schreiber, *Science,* 251:283–287 (1991), McKeon, *Cell,* 66:823–826, (1991), Friedman and Weissman, *Cell,* 66:799–806, (1991), Liu et al., *Cell,* 66:807–815 (1991)). For example, the inducer binding portion of the immunophilin, FKBP12, which can be clustered in the cytoplasm by the addition of FK1012, a synthetic dimeric form of the immunosuppressant FK506 (Spencer et al., *Science* 262: 1019–1024 (1993) can be used as an ICD.

The transmembrane domain may be contributed by the protein contributing the multispecific extracellular inducer clustering domain, the protein contributing the effector function signaling domain, the protein contributing the proliferation signaling portion, or by a totally different protein. For the most part it will be convenient to have the transmembrane domain naturally associated with one of the domains. In some cases it will be desirable to employ the transmembrane domain of the ζ, η or FcεR1γ chains which contain a cysteine residue capable of disulfide bonding, so that the resulting chimeric protein will be able to form disulfide linked dimers with itself, or with unmodified versions of the ζ, η or FcεR1γ chains or related proteins. In some instances, the transmembrane domain will be selected or modified by amino acid substitution to avoid binding of such domains to the transmembrane domains of the same or different surface membrane proteins to minimize interactions with other members of the receptor complex. In other cases it will be desirable to employ the transmembrane domain of ζ, η, FcεR1-γ and -β, MB1 (Igα), B29 or CD3-γ, ζ, or ε, in order to retain physical association with other members of the receptor complex.

Extracellular inducer molecules employed in the present invention can be antigens which bind the immunoglobulin-derived ECDs, described above. These may include viral proteins, (e.g. gp120 and gp41 envelope proteins of HIV, envelope proteins from the Hepatitis B and C viruses, the gB and other envelope glycoproteins of human cytomegalovirus, the envelope proteins from the Kaposi's sarcoma-associated herpesvirus), and surface proteins found on cancer cells in a specific or amplified fashion, (e.g. the IL-14 receptor, CD 19 and CD 20 for B cell lymphoma, the Lewis Y and CEA antigens for a variety of carcinomas, the Tag72 antigen for breast and colorectal cancer, EGF-R for lung cancer, and the HER-2 protein which is often amplified in human breast and ovarian carcinomas). For other receptors, the receptors and ligands of particular interest are CD4, where the ligand is the HIV gp120 envelope glycoprotein, and other viral receptors, for example ICAM, which is the receptor for the human rhinovirus, and the related receptor molecule for poliovirus.

The intracellular inducer molecules employed in the present invention must be molecules which can be delivered to the cytoplasm. For example, the inducer may be lipophilic, or be transported into the cell by active transport or pinocytosis, by fusion with a liposome carrying the inducer, or by semi-permeabilization of the cell membrane. The intracellular inducers cluster the ICDs which make up the CIPRs of the present invention. Examples of inducers include, but are not limited to synthetic dimeric molecules such as FK1012 (Spencer et al., *Science,* 262:1019–1024 (1993)) or dimeric derivatives of the binding domains of other immunophilin binding molecules such as cyclosporin, rapamycin and 506BD (Schreiber, *Science,* 251:283–287 (1991), McKeon, *Cell,* 66:823–826, (1991)). Steroids, such as estrogen, progesterone, the androgens, glucocorticoids, thyroid hormone, vitamin D, retinoic acid, 9-cis retinoic acid or ecdysone, or antagonists or derivatives of these molecules may also be used as intracellular inducer molecules. In particular, the steroid antagonist RU 486 may be used (Wang et al., *Proc. Natl. Acad. Sci.,* 91:8180–8184 (1994)).

In some instances, a few amino acids at the joining region of the natural protein domain may be deleted (eg., truncated), usually not more than 30, more usually not more than 20. Also, one may wish to introduce a small number of amino acids at the borders, usually not more than 30, more usually not more than 20 (linkers or the membrane hinge region). The deletion or insertion of amino acids will usually be as a result of the needs of the construction, providing for convenient restriction sites, ease of manipulation, improvement in levels of expression, proper folding of the molecule or the like. In addition, one may wish to substitute one or more amino acids with a different amino acid (i.e., a modification) for similar reasons, usually not substituting more than about five amino acids in any one domain. The PSDs and EFSDs will generally be from about 50 to 1500 amino acids, depending upon the particular domain employed, while the transmembrane domain will generally have from about 20 to 35 amino acids. The individual ECDs will generally be from about 50 to 1500 amino acids, depending on the particular domain employed. The MSECDs will usually contain between two and twenty ECDs, more preferably between two and ten ECDs, and most preferably between two and five ECDs.

Normally, the signal sequence at the 5' terminus of the open reading frame (ORF) which directs the chimeric protein to the surface membrane will be the signal sequence of the ECD. However, in some instances, one may wish to exchange this sequence for a different signal sequence. However, since the signal sequence will be removed from the protein during processing, the particular signal sequence will normally not be critical to the subject invention.

The chimeric construct, which encodes the chimeric protein according to this invention will be prepared in conventional ways. Since, for the most part, natural sequences may be employed, the natural genes may be isolated and manipulated, as appropriate, so as to allow for the proper joining of the various domains. Thus, one may prepare the truncated portion of the sequence by employing the polymerase chain reaction (PCR), using appropriate primers which result in deletion of the undesired portions of the gene. Alternatively, one may use primer repair, where the sequence of interest may be cloned in an appropriate host. In either case, primers may be employed which result in termini, which allow for annealing of the sequences to result in the desired open reading frame encoding the chimeric protein. Thus, the sequences may be selected to provide for restriction sites which are blunt-ended, or have complementary overlaps.

If desired, the multispecific extracellular domain may also include the transcriptional initiation region, which will allow for expression in the target host. Alternatively, one may wish to provide for a different transcriptional initiation region, which may allow for constitutive or inducible expression, depending upon the target host, the purpose for the introduction of the subject chimeric protein into such host, the level of expression desired, the nature of the target host, and the like. Thus, one may provide for expression upon differentiation or maturation of the target host, activation of the target host, or the like.

A wide variety of promoters have been described in the literature, which are constitutive or inducible, where induction may be associated with a specific cell type or a specific level of expression. Alternatively, a number of viral promoters are known which may also find use. Promoters of interest include the β-actin promoter, SV40 early and late promoters, immunoglobulin promoter, human cytomegalovirus promoter, and the Friend spleen focus-forming virus promoter. The promoters may or may not be associated with enhancers, where the enhancers may be naturally associated with the particular promoter or associated with a different promoter.

The sequence of the open reading frame may be obtained from genomic DNA, cDNA, or be synthesized, or combinations thereof. Depending upon the size of the genomic DNA and the number of introns, one may wish to use cDNA or a combination thereof. In many instances, it is found that introns stabilize the mRNA. Also, one may provide for non-coding regions which stabilize the mRNA.

A termination region will be provided 3' to the cytoplasmic domain, where the termination region may be naturally associated with the cytoplasmic domain or may be derived from a different source. For the most part, the termination regions are not critical and a wide variety of termination regions may be employed without adversely affecting expression.

The various manipulations may be carried out in vitro or may be introduced into vectors for cloning in an appropriate host, e.g., *E. coli.* Thus, after each manipulation, the resulting construct from joining of the DNA sequences may be cloned into an expression vector. The sequence may be screened by restriction analysis, sequencing, or the like to insure that it encodes the desired chimeric protein.

The chimeric construct may be introduced into the target cell in any convenient manner. Techniques include calcium phosphate or DEAE-dextran mediated DNA transfection, electroporation, protoplast fusion, liposome fusion, biolistics using DNA-coated particles, and infection, where the chimeric construct is introduced into an appropriate virus (e.g. retrovirus, adenovirus, adeno-associated virus, Herpes virus, Sindbis virus, papilloma virus), particularly a non-replicative form of the virus, or the like. In addition, direct injection of naked DNA or protein- or lipid-complexed DNA may also be used to introduce DNA into cells.

Once the target host has been transformed, integration will usually result. However, by appropriate choice of vectors, one may provide for episomal maintenance. A large number of vectors are known which are based on viruses, where the copy number of the virus maintained in the cell is low enough to maintain the viability of the cell. Illustrative vectors include SV40, EBV and BPV.

It is also contemplated that the introduction of the chimeric constructs of the present invention into cells may result in the transient expression of the MSCRs. Such transient expression may be preferable if a short-term therapeutic effect is desired. Unstable replication or the absence of DNA replication may result, for example, from adenovirus infection or transformation with naked DNA.

The MSCRs of the present invention are employed in a wide variety of target host cells, normally cells from vertebrates, more particularly, mammals, desirably domestic animals or primates, particularly humans. In particular, the subject invention may also find application in regulating the expansion and effector activity of lymphoid cells, e.g., T lymphocytes (including CD8+ T cells, CD4+ T cells, cytotoxic T cells and helper T cells), B lymphocytes, cytotoxic lymphocytes (CTL), natural killer cells (NK), tumor-infiltrating-lymphocytes (TIL) or other cells which are capable of killing target cells when activated. In addition, suitable host cells in which to introduce MSCRs of the present invention include hematopoietic stem cells, which develop into cytotoxic effector cells with both myeloid and lymphoid phenotype including granulocytes, mast cells, basophils, macrophages, natural killer (NK) cells and T and B lymphocytes.

Once one has established that the transformed host cell expresses the MSCRs of the present invention in accordance with the desired regulation and at a desired level, one may then determine whether the MSCPRs or hybrid MSCRs are functional in the host cell in providing for the desired proliferation signal. One may use established methodology for measuring proliferation to verify the functional capability of the above MSCRs. The proliferative response of cells can be measured by a variety of techniques known to those skilled in the art. For example, DNA synthesis can be measured by the incorporation of either tritiated thymidine or orotic acid. The incorporation of bromodeoxyuridine into newly synthesized DNA can be measured by immunological staining and the detection of dyes, or by ELISA (Enzyme-linked immunosorbent assay)(Doyle et al., *Cell and Tissue Culture: Laboratory Procedures,* Wiley, Chichester, England, (1994)). The mitotic index of cells can be determined by staining and microscopy, by the fraction labeled mitoses method or by FACS analysis (Doyle et al., supra, (1994); Dean, *Cell Tissue Kinet.* 13:299–308 (1980); Dean, *Cell Tissue Kinet.* 13:672–681 (1980)). The increase in cell size which accompanies progress through the cell cycle can be measure by centrifugal elutriation (Faha et al., *J Virol.* 67:2456–2465 (1993)). Increases in the number of cells may also be measured by counting the cells, with or without the addition of vital dyes. In addition, signal transduction can also be measured by the detection of phosphotyrosine, the in vitro activity of tyrosine kinases from activated cells, c-myc induction, and calcium mobilization as described in the Examples below. In the case of MSCRs containing EFSDs, one may determine whether the host cell has been provided with an effector signal in a variety of ways well known to those skilled in the art, depending on the EFSD and the cell type. For example, the activity of MSCEFRs and hybrid MSCRs in signaling cytotoxic effector function in engineered cytotoxic T cells can be measured by the release of $^{51}$Cr from labeled cells displaying extracellular inducer molecules, while the activity of MSCEFRs and hybrid MSCRs in signaling helper effector function in engineered helper T cells can be measured by the release of cytokines in the presence of inducer.

In the present invention, a host cell may express two different MSCRs, one containing an effector function signaling domain and the other containing a proliferation signaling domain (i.e. MSCEFR and MSCPR). Both MSCRs may contain the same MSECDs. Alternatively, a host cell may express a hybrid MSCR combining both signaling domains (EFSD and PSD) on the same chain. In both situations, the binding of an extracellular inducer molecule to the MSECD will stimulate host cells to act as therapeutic agents at the same time they are expanding in response to binding to an extracellular inducer molecule, e.g., gp120 for HIV or cancer-specific antigens.

The specific targets of cells expressing the multispecific chimeric receptors (MSCRs) of the present invention include diseased cells, such as cells infected with HIV, HTLV-I or II, cytomegalovirus, hepatitis A, B or C viruses, *Mycobacterium avium, Mycobacterium tuberculosis, Mycobacterium leprae* etc., neoplastic cells, or autoimmune disease-causing cells where the diseased cells have a surface marker associated with the diseased state. Since MSCRs of the present invention have more than one antigen-binding and/or ligand-binding domain, the present invention may have advantages over monospecific chimeric receptors in treating human diseases such as infectious disease, cancer and autoimmune disease. The application of the present invention for targeting more than one epitope of a given pathogen, more than one pathogen, or a heterogeneous population of disease-causing cells that may be found in malignant or autoimmune disease, is designed to have the therapeutic benefit of a combination therapy, while having the safety profile and pharmacological properties of a single therapeutic agent.

The MSCRs of the present invention are envisioned as a strategy for overcoming the ability of viruses such as HIV to become drug-resistant, and may be applicable in treating other diseases in which drug-resistance or antigenic variation is a significant problem (eg. cancer, bacterial and parasitic infections). Through the application of the present invention, the probability that a given viral variant will eventually arise which is not targeted by a chimeric receptor expressing cell would decrease in direct relation to the number of antigenic specificities recognized by the multispecific chimeric receptor. In particular, single-chain antibodies which recognize many different HIV antigens can be employed to create MSCRs to use as anti-AIDS therapeutics. Similar strategies can be applied for other types of pathogens, such as chronic or recurrent bacterial infections, for which the the problem of drug resistance in the face of ongoing antibiotic therapy is particularly acute.

The MSCRs of the present invention may also be useful in the development of chimeric receptor-expressing cells for the treatment of multiple infections. For example, an MSCR-containing T cell which recognizes HIV as well as another opportunistic pathogen such as CMV, herpesviruses, etc. can also be used as an anti-AIDS therapeutic. Since immunocompromised individuals are also susceptible to various bacterial infections, neutrophils may also be armed with multispecific chimeric receptors which recognize the major classes of relevant pathogens.

The MSCRs of the present invention may also be useful in treating viral and bacterial infections where antigenic variation and the existence of multiple strains has limited traditional, single agent therapies. For example, MSCRs containing MSECDs which recognize multiple antigens or epitopes from a single pathogen can be used to treat HIV, hepatitis A, B and C viruses, Kaposi's sarcoma-associated herpes virus, Herpes Simplex viruses, Herpes Zoster virus, CMV, papilloma virus, respiratory syncytial virus, and influenza viruses.

The MSCR-containing immune cells of the present invention may also find application in cancer therapy, since resistance to chemotherapeutic agents has been an important obstacle in the successful use of traditional treatment regimens and combination chemotherapy has been limited by the significant side effects of these agents and the development of multidrug resistance. In addition, the high growth rate of malignant cells increases the potential for the selection of antigenic variants or for resistance due to antigen or epitope loss. As an example, B cell lymphoma can be treated with MSCRs which recognize more than one pan-B cell surface marker such as CD19, CD20 or CD22, and/or markers specific for malignant but not resting B cells, such as the interleukin-14 receptor.

The present invention may also be useful as a cancer therapy in the MSCR's ability to target cytotoxic cells to cancers such as melanoma in which the host can mount a tumor antigen-specific T cell response. The availability of CTL clones from patients to MHC-restricted epitopes on melanoma has permitted the molecular analysis of the T cell receptors responsible for tumor killing (Mandelboim et al., *Nature,* 369:67–71 (1994); Cox et al., *Science,* 264:716–719 (1994)). However, in employing a single-chain T cell receptor (scTCR) of sufficient affinity to redirect cytolysis, a given chimeric receptor would still be MHC-restricted and active in only a small fraction of the patient population. Multispecific scTCR's could be developed which would recognize the relevant tumor-specific peptide antigen in the context of many HLA haplotypes. Such 'semi-universal' receptors may be capable of dealing with a particular disease target in most affected individuals.

The MSCR technology may also be used to treat autoimmune disorders such as multiple sclerosis, rheumatoid arthritis, type 1 diabetes mellitus, myasthenia gravis and Graves' disease, where the autoreactive T cells and/or B cells are oligo- or polyclonal. Immune cells bearing MSCRs which recognize the members of the restricted T cell receptor (TCR) repertoire expressed by the disease-causing autoreactive T cells can be used to treat autoimmune disease. In particular, restricted TCR expression has been observed for the T cells found at the sites of disease in multiple sclerosis (brain) (Oksenberg et al., *Proc. Natl. Acad. Sci,* 86:988–992 (1989)) and rheumatoid arthritis (joint synovium) (Stamenkovic et al., *Proc. Natl. Acad. Sci.,* 85:1179–1183 (1988)).

High-titer retroviral producer lines are used to transduce the chimeric proliferation receptor constructs into autologous or allogeneic human T-cells, hematopoietic stem cells or other cells, described above through the process of retroviral mediated gene transfer as described by Lusky et al. in (1992) *Blood* 80:396. In addition to the gene encoding the chimeric proliferation receptor, additional genes may be included in the retroviral construct. These include genes such as the thymidine kinase or cytosine deaminase genes (Borrelli et al. (1988) *Proc. Natl. Acad. Sci. USA* 85:7572) which acts as a suicide gene for the marked cells if the patient is exposed to gancyclovir or 5'-fluorouracil (5FU), respectively. Thus, if the percentage of marked cells is too high, gancyclovir or 5FU may be administered to reduce the percentage of cells expressing the chimeric receptors. In addition, if the percentage of marked cells needs to be increased, the multi-drug resistance gene can be included (Sorrentino et al. (1992) *Science* 27:99) which functions as a preferential survival gene for the marked cells in the patients if the patient is administered a dose of a chemotherapeutic agent such as taxol. Therefore, the percentage of marked cells in the patients can be titrated to obtain the maximum therapeutic benefit.

In addition, high-titer retroviral, adenoviral or other viral or non-viral producer lines may be used to transduce the chimeric proliferation receptor constructs into autologous or allogeneic nerve cells, hematopoietic cells including stem cells, islets of Langerhans, keratinocytes, muscle cells or other cells following the methods of retroviral, adenoviral or other viral or non-viral mediated gene transfer as described in Finer et al., *Blood* 83:43–48 (1994) and U.S. patent application Ser. No. 08/333,680. Similar to the procedure described above, other genes may be included in the retroviral, adenoviral or other viral or non-viral constructs in addition to the chimeric proliferation receptor in the recipient cell. After introduction of the construct into the cell type of interest, the cells may be expanded in an appropriate medium well known in the art and used in a variety of ways previously described.

The following examples are by way of illustration and not by way of limitation.

EXAMPLES

Example 1

Multispecific antibodies comprising multiple antibody extracellular clustering domains and an Ig-Fc effector function domain.

Multispecific antibodies were created which contain two or more extracellular clustering domains (ECDs) which are derived from antibodies and/or single-chain antibodies, or modifications thereof. The constructs described in this example contain two SCFv domains which were derived from the 98.6 human monoclonal antibody (Mab), which is specific for the HIV-1 gp41 envelope glycoprotein, and the 447D human MAb, which is specific for the HIV-1 gp120 envelope glycoprotein. The 98.6 light-linker-heavy (LLH) SCFv consists of (from N- to C-terminus): 1) the Vκ signal sequence and VK variable domain (residues 1–107 of the mature protein) of the 98.6 MAb, 2) the 14 amino acid L212 peptide linker (Gly-Ser-Thr-Ser-Gly-Ser-Gly-Lys-Ser-Ser-Glu-Gly-Lys-Gly) (SEQ ID NO:23) (Bedzyk et al *J.Biol Chem.* (1990) 265: 18615–18620), and 3) the VH variable domain (residues 1–113 of the mature protein) of the 98.6 MAb. The 447D light-linker-heavy (LLH) SCFv consists of (from N- to C-terminus): 1) the Vλ signal sequence and Vλ variable domain (residues 1–107 of the mature protein) of the 447D MAb, 2) the 14 amino acid L212 peptide linker, and 3) the VH variable (residues 1–113 of the mature protein) of the 447D MAb. Alternatively, the 98.6 and 447D SCFv's are created as heavy-linker-light (HLL) constructs in which the heavy chain variable domain precedes the light chain variable domain, connected by a suitable oligo- or polypeptide linker. Both LLH or HLL SCFv derivatives of the 98.6 and 447D MAbs may be constructed using a variety of oligo- and polypeptide linkers. In this example, the 98.6 LLH SCFv was joined at its C-terminus (residue 113 of the VH variable domain) to the N-terminus of the 447D LLH SCFv (residue 1 of the Vλ variable domain). Alternatively, the 447D LLH SCFv is joined at its C-terminus (residue 113 of the VH variable domain) to the N-terminus of the 98.6 LLH SCFv (residue 1 of the Vκ variable domain). Either LLH SCFv may be substituted for by the corresponding HLL SCFv, or modifications thereof. The two SCFv's were joined either directly, or via an oligo- or polypeptide linker. The C-terminus of the second SCFv was fused in turn to the hinge and Fc region (residues 226–478) of the human IgG2 heavy chain. Mammalian expression vectors for the 98.6 SCFv/447D SCFv multispecific antibodies described in this example were constructed using plasmid pMSAb1int. This intermediate plasmid was constructed from three DNA fragments: 1) a 3.9 kb vector fragment obtained by digestion of pIK1.1 with EcoRI and SfiI, 2) a 1.0 kb fragment encoding the 98.6 LLH SCFv domain, obtained by digestion of pIK98.6KLHγ2 with PmlI, modification of the cohesive end with T4 DNA polymerase and dNTPs to create a blunt end, followed by digestion with EcoRI, and 3) a 1.9 kb fragment encoding the 447D LLH SCFv domain and the human IgG2 hinge and Fc domains, obtained by digestion of pIK447DLLHγ2 with EcoRI, modification of the cohesive end with T4 DNA polymerase and dNTPs to create a blunt end, followed by digestion with SfiI. pMSAb1int was identified by restriction enzyme analysis and used to prepare single-stranded DNA template for oligonucleotide-directed mutagenesis. In each example, the correct expression plasmid was identified by restriction mapping and its structure was confirmed by DNA sequencing.

Example 1A

SAb(αgp41)-SAb(αgp120)-Fc pIK-SAb(αgp41)-SAb(αgp120)-Fc directs the expression of a hybrid protein consisting of the Vκ signal sequence and SCFv domain of 98.6-LLH joined at its C-terminus (98.6-VH residue 113) to the N-terminus of the SCFv domain of 447D-LLH (447D-Vλ residue 1), followed by the human IgG2 hinge and Fc domains (residues 226–478). This plasmid is constructed by oligonucleotide-directed mutagenesis using single-stranded pMSAb1int DNA as the template with oligonucleotide 1 (SEQ ID NO:1) as the primer. The correct expression plasmid was identified by colony hybridization using oligonucleotide 2 (SEQ ID NO:2) as a probe.

Example 1B

SAb(αgp41)-L1-SAb(αgp120)-Fc pIK-SAb(αgp41)-L1-SAb(αgp120)-Fc directs the expression of a hybrid protein consisting of the Vκ signal sequence and SCFv domain of 98.6-LLH joined at its C-terminus (98.6-VH residue 113) by a 14 amino acid linker (Gly-Ser-Thr-Ser-Gly-Ser-Gly-Lys-Ser-Ser-Glu-Gly-Lys-Gly) (SEQ ID NO:23) to the N-terminus of the SCFv domain of 447D-LLH (447D-Vλ residue 1), followed by the human IgG2 hinge and Fc domains (residues 226–478). This plasmid is constructed by oligonucleotide-directed mutagenesis using single-stranded pMSAb1int DNA as the template with oligonucleotide 3 (SEQ ID NO:3) as the primer. The correct expression plasmid was identified by colony hybridization using oligonucleotide 4 (SEQ ID NO:4) as a probe.

Example 1C

SAb(αgp41)-L2-SAb(αgp120)-Fc pIK-SAb(αgp41)-L2-SAb(αgp120)-Fc directs the expression of a hybrid protein consisting of the Vκ signal sequence and SCFv domain of 98.6-LLH joined at its C-terminus (98.6-VH residue 113) by a 25 amino acid linker (Ser-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Gly) (SEQ ID NO:24) to the N-terminus of the SCFv domain of 447D-LLH (447D-Vλ residue 1), followed by the human IgG2 hinge and Fc domains (residues 226–478). This plasmid is constructed by oligonucleotide-directed mutagenesis using single-stranded pMSAb1int DNA as the template with oligonucleotide 5 (SEQ ID NO:5) as the primer. The correct expression plasmid was identified by colony hybridization using oligonucleotide 6 (SEQ ID NO:6) as a probe.

Example 1D

SAb(αgp41)-L3-SAb(αgp120)-Fc pIK-SAb(αgp41)-L3-SAb(αgp120)-Fc directs the expression of a hybrid protein consisting of the Vκ signal sequence and SCFv domain of 98.6-LLH joined at its C-terminus (98.6-VH residue 113) by a 10 amino acid linker (Asp-Lys-Thr-His-Thr-Ser-Pro-Pro-Ser-Pro) (SEQ ID NO:25) to the N-terminus of the SCFv domain of 447D-LLH (447D-Vλ residue 1), followed by the human IgG2 hinge and Fc domains (residues 226–478). This plasmid is constructed by oligonucleotide-directed mutagenesis using single-stranded pMSAb1int DNA as the template with oligonucleotide 7 (SEQ ID NO:7) as the primer. The correct expression plasmid was identified by colony hybridization using oligonucleotide 8 (SEQ ID NO:8) as a probe.

Example 1E

SAb(αgp41)-L4-SAb(αgp120)-Fc pIK-SAb(αgp41)-L4-SAb(αgp120)-Fc directs the expression of a hybrid protein consisting of the Vκ signal sequence and SCFv domain of 98.6-LLH joined at its C-terminus (98.6-VH residue 113) by an 18 amino acid linker (Glu-Leu-Gln-Leu-Glu-Glu-Ser-Ser-Ala-Glu-Ala-Gln-Asp-Gly-Glu-Leu-Asp) (SEQ ID NO:26) to the N-terminus of the SCFv domain of 447D-LLH (447D-Vλ residue 1), followed by the human IgG2 hinge and Fc domains (residues 226–478). This plasmid is constructed by oligonucleotide-directed mutagenesis using single-stranded pMSAb1int DNA as the template with oligonucleotide 9 (SEQ ID NO:9) as the primer. The correct expression plasmid was identified by colony hybridization using oligonucleotide 10 (SEQ ID NO:10) as a probe.

Example 2

Multispecific antibodies comprising an antibody extracellular clustering domain, a ligand-receptor (CD4) extracellular clustering domain, and an Ig-Fc effector function domain.

Multispecific antibodies were created which contain two or more extracellular clustering domains (ECDs), at least one of which is derived from an antibody and/or single-chain antibody, or modifications thereof, and at least one of which is derived from a ligand-receptor binding domain, or modifications thereof. The constructs described in this example contain the 447D LLH SCFv domain (described in example 1), and the human CD4 V1 & V2 domains, which bind with high affinity to the HIV-1 gp120 envelope glycoprotein. Alternatively, the 447D SCFv's are created as HLL constructs in which the heavy chain variable domain precedes the light chain variable domain, connected by a suitable oligo- or polypeptide linker. Both LLH or HLL SCFv derivatives of the 447D MAb may be constructed using a variety of oligo- and polypeptide linkers. Other portions of CD4 may be employed in such constructs including the entire CD4 EXT domain (residues 1–371 of the mature polypeptide) as well as various truncations and/or modifications thereof. In this example, the 447D LLH SCFv was joined at its C-terminus (residue 113 of the VH variable domain) to the N-terminus of the CD4 protein (residue 1 of the mature polypeptide). Alternatively, the CD4 protein is joined at the C-terminus of its EXT domain (residue 371 of the mature polypeptide, or truncations thereof, e.g. residue 180 which resides at the C-terminus of the CD4 V1 & V2 domains) to the N-terminus of the 447 LLH SCFv (residue 1 of the Vλ variable domain). The 447D LLH SCFv may be substituted for by the corresponding HLL SCFv, or modifications thereof. The 447D LLH SCFv was joined to the CD4 protein either directly, or via an oligo- or polypeptide linker. The C-terminus of the CD4 V1 & V2 domains, was fused in turn to the hinge and Fc region (residues 226–478) of the human IgG2 heavy chain. Mammalian expression vectors for the 447D SCFv/CD4 V1V2 multispecific antibodies described in this example were constructed using plasmid pMSAb2int. This intermediate plasmid was constructed from three DNA fragments: 1) a 3.9 kb vector fragment obtained by digestion of pIK1.1 with EcoRI and SfiI, 2) a 1.0 kb fragment encoding the 447D LLH SCFv domain, obtained by digestion of pIK447DLLHγ2 with PmlI, modification of the cohesive end with T4 DNA polymerase and dNTPs to create a blunt end, followed by digestion with EcoRI, and 3) a 1.9 kb fragment encoding the CD4 V1 & V2 domains linked at their C-terminus to the hinge and Fc regions of the human IgG2 heavy chain, obtained by digestion of pIKCD4γ2 with EcoRI, modification of the cohesive end with T4 polymerase and dNTPs to create a blunt end, followed by digestion with SfiI. pMSAb2int was identified by restriction analysis, and used to prepare single-stranded DNA template for oligonucleotide-directed mutagenesis. In each example, the correct expression plasmid was identified by restriction mapping and its structure was confirmed by DNA sequencing.

Example 2A

SAb(αgp120)-CD4-Fc pIK-SAb(αgp120)-CD4-Fc directs the expression of a hybrid protein consisting of the Vλ signal sequence and SCFv domain of 447D-LLH joined at its C-terminus (447D-VH residue 113) to the N-terminus of human CD4 (residues 1–180 of the mature polypeptide), followed by the human IgG2 hinge and Fc domains (residues 226–478). This plasmid is constructed by oligonucleotide-directed mutagenesis using single stranded pMSAb2int DNA as the template with oligonucleotide 11 (SEQ ID NO:12) as the primer. The correct expression plasmid was identified by colony hybridization using oligonucleotide 12 (SEQ ID NO:12)as a probe.

Example 2B

SAb(αgp120)-L1-CD4-Fc pIK-SAb(αgp120)-L1-CD4-Fc directs the expression of a hybrid protein consisting of the Vλ signal sequence and SCFv domain of 447D-LLH joined at its C-terminus (447D-VH residue 113) by a 14 amino acid linker (Gly-Ser-Thr-Ser-Gly-Ser-Gly-Lys-Ser-Ser-Glu-Gly-Lys-Gly) (SEQ ID NO:23) to the N-terminus of human CD4 (residues 1–180 of the mature polypeptide), followed by the human IgG2 hinge and Fc domains (residues 226–478). This plasmid is constructed by oligonucleotide-directed mutagenesis using single stranded pMSAb2int DNA as the template with oligonucleotide 13 (SEQ ID NO:13)as the primer. The correct expression plasmid was identified by colony hybridization using oligonucleotide 4 (SEQ ID NO:4)as a probe.

Example 2C

SAb(αgp120)-L2-CD4-Fc pIK-SAb(αgp120)-L2-CD4-Fc directs the expression of a hybrid protein consisting of the Vλ signal sequence and SCFv domain of 447D-LLH joined at its C-terminus (447D-VH residue 113) by a 25 amino acid linker (Ser-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Gly) (SEQ ID NO:24) to the N-terminus of human CD4 (residues 1–180 of the mature polypeptide), followed by the human IgG2 hinge and Fc domains (residues 226–478). This plasmid is constructed by oligonucleotide-directed mutagenesis using single stranded pMSAb2int DNA as the template with oligonucleotide 14 (SEQ ID NO:14)as the primer. The correct expression plasmid was identified by colony hybridization using oligonucleotide 6 (SEQ ID NO:6)as a probe.

Example 2D

SAb(αgp120)-L3-CD4-Fc pIK-SAb(αgp120)-L3-CD4-Fc directs the expression of a hybrid protein consisting of the Vλ signal sequence and SCFv domain of 447D-LLH joined at its C-terminus (447D-VH residue 113) by a 10 amino acid linker (Asp-Lys-Thr-His-Thr-Ser-Pro-Pro-Ser-Pro) (SEQ ID NO:25) to the N-terminus of human CD4 (residues 1–180 of the mature polypeptide), followed by the human IgG2 hinge and Fc domains (residues 226–478). This plasmid is constructed by oligonucleotide-directed mutagenesis using single stranded pMSAb2int DNA as the template with oligonucleotide 15 (SEQ ID NO:15) as the primer. The correct expression plasmid was identified by colony hybridization using oligonucleotide 8 (SEQ ID NO:8) as a probe.

Example 2E

SAb(αgp120)-L4-CD4-Fc pIK-SAb(αgp120)-L4-CD4-Fc directs the expression of a hybrid protein consisting of the Vλ signal sequence and SCFv domain of 447D-LLH joined at its C-terminus (447D-VH residue 113) by an 18 amino acid linker (Glu-Leu-Gln-Leu-Glu-Glu-Ser-Ser-Ala-Glu-Ala-Gln-Asp-Gly-Glu-Leu-Asp) (SEQ ID NO:26) to the N-terminus of human CD4 (residues 1–180 of the mature polypeptide), followed by the human IgG2 hinge and Fc domains (residues 226–478). This plasmid is constructed by oligonucleotide-directed mutagenesis using single stranded pMSAb2int DNA as the template with oligonucleotide 16 (SEQ ID NO:16) as the primer. The correct expression plasmid was identified by colony hybridization using oligonucleotide 10 (SEQ ID NO:10) as a probe.

Example 3

Expression & characterization of multispecific antibodies

To determine whether each multispecific antibody can be efficiently expressed and secreted, and thus properly folded, each corresponding mammalian expression vector was transfected into a model mammalian cell, using the human 293 embryonic kidney cell line (ATCC CRL 1573). Following transfection, the expression and corresponding apparent molecular mass of each polypeptide was evaluated by radio-immunoprecipitation (RIP), and the level of secretion was quantitated using an enzyme-linked immunosorbent assay (ELISA).

Example 3A

Transfection of human 293 cells with multispecific antibody expression vectors.

For transfection, 293 cells were grown in DMEM:F12 media (JRH Biosciences) containing 10% fetal calf serum, and passaged at a 1:8 to 1:12 split ratio every 3 to 4 days. Forty-eight hours prior to transfection, cells were plated by passaging the contents of one subconfluent 10 cm tissue culture dish onto twenty 6 cm tissue culture dishes. Five µg of each expression plasmid DNA was transfected onto a 6 cm dish by the calcium phosphate coprecipitation method (Wigler et al. (1979) Cell 16:777). Sixteen hours after transfection, the transfected cells were fed with fresh complete medium. The expression of multispecific antibody polypeptides was evaluated by RIP analysis and ELISA at 48 hours post-transfection.

Example 3B

Figure 3:
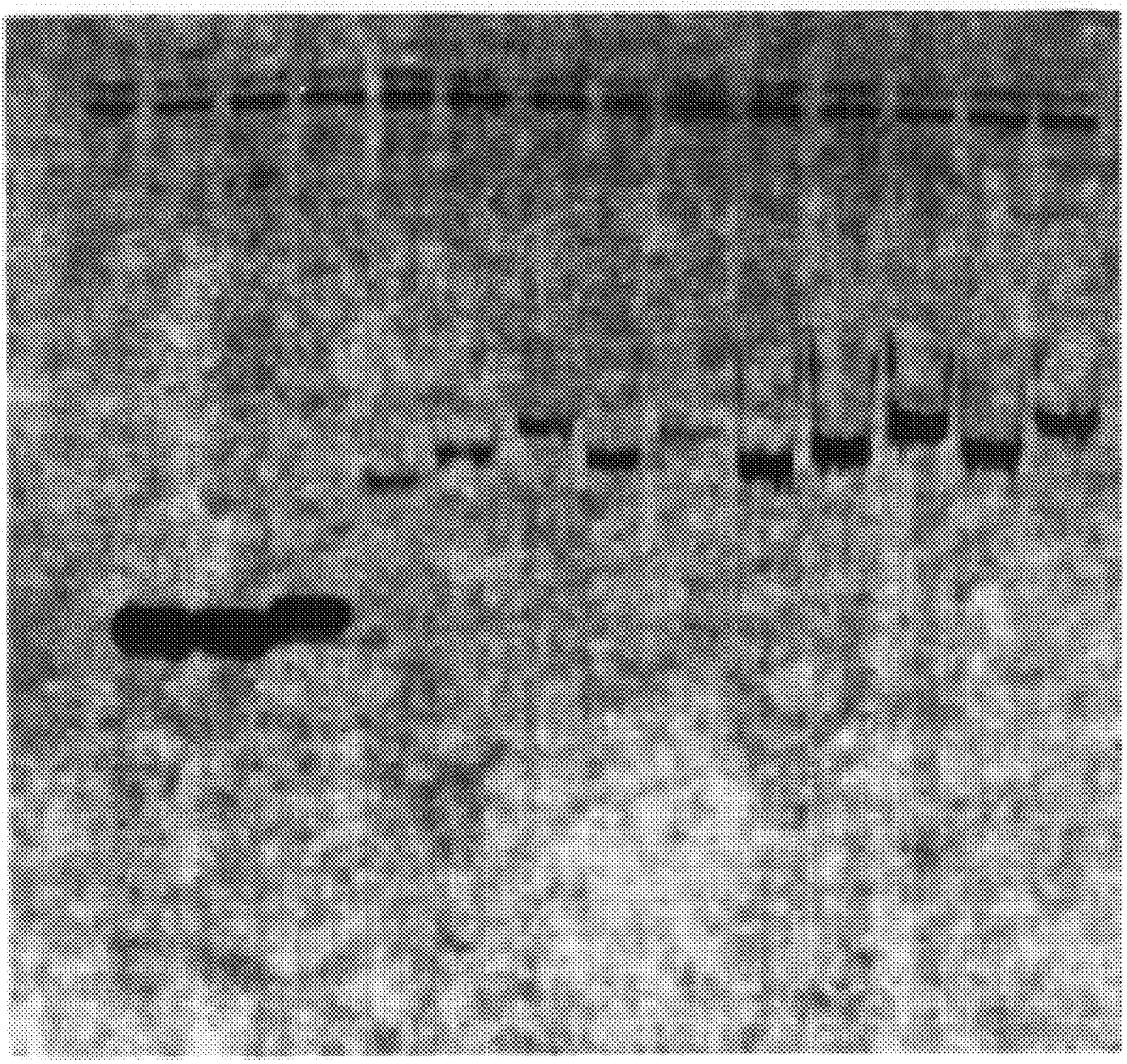
FIG. 3 is an autoradiogram of immunoprecipitations of culture supernatants from 293 cells transfected with the following monospecific and multispecific antibody constructs as described in Examples 1 and 2: lane a, CD4-Fc; lane b, SAb(αgp41)-Fc; lane c, SAb(αgp120)-Fc; lane d, SAb(gp41)-SAb(αgp120)-Fc; lane e, SAb(αgp41)-L1-SAb(αgp120)-Fc; lane f, SAb(αgp41)-L2-SAb(αgp120)-Fc; lane g, SAb(αgp41)-L3-SAb(αgp120)-Fc; lane h, SAb(αgp41)-L4-SAb(αgp120)-Fc; lane i, SAb(αgp120)-CD4-Fc; lane j, SAb(αgp120)-L1-CD4-Fc; lane k, SAb(αgp120)-L2-CD4-Fc; lane 1, SAb(αgp120)-L3-CD4-Fc; lane m, SAb(αgp120)-L4-CD4-Fc.

Radioimmunoprecipitation analysis of multispecific antibodies expressed in transfected 293 cells Forty hours after transfection, 293 cells were fed with 2 ml of methionine- and cysteine-deficient RPMI media containing 10% dialysed fetal calf serum, supplemented with [35S]-methionine and [35S]-cysteine (Tran35Slabel, 1160 Ci/mMol, ICN Biomedicals, Inc., Irvine, Calif.). Cells were cultured for an additional 8 hours, the conditioned medium harvested, and the labelled cells lysed in RIPA buffer (50 mM Tris pH 7.5, 150 mM NaCl, 1% Triton X-100, 0.5% sodium deoxycholate, 0.1% sodium dodecyl sulfate (SDS)). For radio-immunoprecipitation, labelled conditioned medium was mixed with an equal volume of 2X RIPA buffer. 35S-labelled multispecific antibodies, which bind to the Staphylococcus aureus Protein A via their IgG2 Fc domain, were then precipitated with 10 µl Pansorbin (Calbiochem, La Jolla, Calif.). Immunoprecipitates were washed three times in RIPA buffer and once in distilled water, and boiled for several minutes in SDS sample buffer (50 mM Tris-HCl, pH 6.8, 150 mM β-mercaptoethanol, 2% SDS, 10% glycerol). Immunoprecipitates were also analysis following boiling in non-reducing SDS sample buffer (lacking β-mercaptoethanol). Samples were analysed by 10% SDS polyacrylamide gel electrophoresis (SDS-PAGE). Gels were fixed in 20% methanol and 10% acetic acid, soaked in Enlightening solution (NEN Research Products, Boston, MA) for 15 minutes, dried and subjected to autoradiography. This analysis revealed that multispecific antibodies of the predicted molecular mass are expressed and secreted into the culture medium (FIG. 3). Samples analysed by SDS-PAGE under non-denaturing conditions revealed multispecific antibodies with the molecular mass expected for the corresponding homodimeric proteins.

Example 3C

ELISA analysis of multispecific antibodies secreted by transfected 293 cells

Human 293 cells were transfected as described above and were fed fresh medium 16 hours later. Forty-eight hours after transfection the conditioned medium from the transfected cells was harvested and analysed by ELISA. Nunc Maxisorp microtiter plates (Nunc Inc., Naperville, Ill.) were coated for 16 hours at 4° C. with an (Fab')2 fragment derived from a rabbit anti-human IgG polyclonal antisera (Accurate Chemical and Scientific Corporation Westbury, N.Y.), that was diluted 1:1000 in 0.05 M sodium carbonate buffer pH 9.6. Plates were then washed three times in PBS containing 0.05% Tween-20 (PBS-Tween), followed by blocking with PBS containing 1% bovine serum albumin (PBSA) at room temperature for 1 hour. Human IgG2 (Calbiochem, La Jolla, Calif.) was employed as a positive control standard in the assays. Samples and standards were diluted in PBSA, added to the antibody-coated plates, and the plates then incubated for 16 hours at 4° C. Plates were washed three times with PBS-Tween, and an enzyme-linked detection antibody was added to the plates and incubated for 1 hour at room temperature. The detection antibody used was horseradish peroxidase-conjugated goat anti-human IgG polyclonal antisera (Boehringer Mannheim Biochemicals, Indianapolis, Ind.) that was diluted 1:50,000 in PBSA. Plates were then washed 3 times with PBS-Tween and an indicator solution consisting of 1.7 mg/ml o-phenylenediamine hydrochloride in 16 mM citrate buffer pH 4.5 was added. Color development was stopped by the addition of 1 M sulfuric acid, and the results read on a UVmax microplate reader (Molecular Devices Corporation, Menlo Park, Calif.). As shown in Table 1, significant levels of each of the multispecific antibodies described in Examples 1A–E and 2A–E were detected in the culture supernatants of transfected 293 cells.

TABLE 1

| Construct | Concentration (µg/ml) |
| --- | --- |
| CD4-Fc | 1.6 |
| SAb(αgp41)-Fc | 1.2 |
| SAb(αgp120)-Fc | 1.3 |
| SAb(αgp41)-SAb(αgp120)-Fc | 0.23 |
| SAb(αgp41)-L1-SAb(αgp120)-Fc | 0.65 |
| SAb(αgp41)-L2-SAb(αgp120)-Fc | 0.75 |
| SAb(αgp41)-L3-SAb(αgp120)-Fc | 0.40 |
| SAb(αgp41)-L4-SAb(αgp120)-Fc | 0.48 |
| SAb(αgp120)-CD4-Fc | 0.05 |
| SAb(αgp120)-L1-CD4-Fc | 0.17 |
| SAb(αgp120)-L2-CD4-Fc | 0.19 |
| SAb(αgp120)-L3-CD4-Fc | 0.10 |
| SAb(αgp120)-L4-CD4-Fc | 0.12 |

Example 4

Ligand/antigen binding properties of multispecific antibodies

Multispecific antibodies based upon the HIV-1 binding domains of CD4 and the 447D and 98.6 MAbs are further characterized for their ability to bind to the HIV-1 gp120 and gp41 proteins which are the proteolytic cleavage products of the gp160env precursor protein, using cell lines which express wild-type gp160env or mutant forms of gp160env in which one or another binding epitope is impaired.

To facilitate this analysis, cell lines are generated which efficiently express surface gp120 and gp41 polypeptides. Mutants of gp160env are generated which have significantly diminished binding to at least one of the ECDs present in a given multispecific antibody to permit detection of binding mediated by the other ECD(s) present. Levels of binding are determined by FACS analysis using the multispecific antibodies to stain the gp160env-expressing cells.

Example 4A

Vectors for efficient expression of HIV-1 gp160env pIKenv+/rev+/tat– is a vector designed to allow the efficient expression of gp160env in mammalian cells, based on the observation that while expression of the rev gene product is essential for efficient expression of gp160env, expression of the tat gene product may be inhibitory (Bird et al. J. Biol. Chem. (1990) 265: 19151–19157). This plasmid was made in two steps. The first step was the construction of pIKenv, which directs the expression of three HIV gene products: env, rev and tat. This plasmid was constructed from two DNA fragments: 1) a 4.3 kb vector fragment obtained by digestion of pIK1.1 with BglII, modification of the cohesive end with T4 DNA polymerase and dNTPs to create a blunt end, followed by digestion with EcoRI, and 2) a 3.1 kb fragment encoding the env, rev and tat gene products of the HXB2 isolate of HIV-1, obtained by digestion of pCMVenv (U.S. Pat. No. 5,359,046) with XhoI, modification of the cohesive end with T4 DNA polymerase and dNTPs to create a blunt end, followed by digestion with EcoRI. pIKenv was identified by restriction analysis, and used in the second step to prepare a single-stranded DNA template for oligonucleotide-directed mutagenesis using oligonucleotide 17 (SEQ ID NO:17)as a primer to remove the initiator methionine codon (ATG) and the adjacent arginine codon (GAG) of the tat gene, and to replace these sequences with a novel PstI site (CTGCAG). The correct plasmid, pIKenv+/rev+/tat–, was identified by colony hybridization using oligonucleotide 18 (SEQ ID NO:18)as a probe and its structure was confirmed by DNA sequencing.

Example 4B
Expression of an HIV-1 gp160env gene with a mutation in the CD4 binding site pIKenvG370R/rev+/tat− directs the expression of a mutant gp160env polypeptide in which Glu-370 is replaced with Arg, which results in a loss of CD4 binding (Olshevsky et al., *J. Virol.* 64: 5701– 5707). This plasmid is constructed by oligonucleotide-directed mutagenesis using single-stranded pIKenv+/rev+/tat− DNA with oligonucleotide 19 (SEQ ID NO:19) as the primer. The correct expression plasmid is identified by colony hybridization using oligonucleotide 20 (SEQ ID NO:20)as a probe, and its structure is confirmed by DNA sequencing.

Example 4C
Expression of an HIV-1 gp160env gene with a mutation in the 447D MAb binding site pIKenvR315Q/rev+/tat− directs the expression of a mutant gp160env polypeptide in which Arg-315 is replaced with Gln, which results in a loss of 447D MAb binding (Gorny et al, *J. Virol.* 66: 7538–7542). This plasmid is constructed by oligonucleotide-directed mutagenesis using single stranded pIKenv+/rev+/tat− DNA with oligonucleotide 21 (SEQ ID NO:21) as the primer. The correct expression plasmid is identified by colony hybridization using oligonucleotide 22 (SEQ ID NO:22) as a probe, and its structure is confirmed by DNA sequencing.

Example 4D
Binding of multispecific antibodies to mutant and wild-type HIV-1 gp160env polypeptides Human 293 cells are transfected with vectors directing the expression of the multispecific antibodies described in Examples 1 & 2, as well as vectors directing the expression of the parent monospecific antibodies (pIKCD4γ2 for CD4-Fc, pIK447D-LLHγ2 for 447D-LLH-Fc, and pIK98.6KLHγ2 for 98.6-LLH-Fc). Supernatants from transfected 293 cells are analysed by ELISA to determine the concentration of the recombinant proteins secreted into the culture medium. Known amounts of each recombinant protein are then used to determine their ability to bind to cell surface-expressed wild-type and mutant gp160env polypeptides, by FACS analysis of human 293 cells which have been transfected with pIKenv+/rev+/tat−, pIKenvG370R/rev+/tat− and pIKenvR315Q/rev+/tat−. Following the binding of each multispecific or monospecific antibody, the cells are stained with FITC-conjugated mouse anti-human IgG MAb (Becton Dickinson Immunocytometry Systems, San Jose, Calif.). The difference in the degree of fluorescence intensity obtained with multispecific antibodies versus each of the parent monospecific antibodies on transfected cells expressing either mutant or wild-type gp160env polypeptides reveals the ability of each ECD contained within a given multispecific antibody to bind to gp160env.

Example 5
MSCRs comprising multiple antibody extracellular clustering domains and a ζ family signaling domain.

Multispecific chimeric receptors (MSCRs) were created from multispecific antibodies which contain two or more extracellular clustering domains (ECDs) derived from antibodies and/or single-chain antibodies, or modifications thereof. The constructs described in this example contain two LLH SCFv domains which were derived from the 98.6 and 447D human MAbs, respectively, as described in Example 1. Alternatively, the 98.6 and 447D SCFv's are created as heavy-linker-light (HLL) constructs in which the heavy chain variable domain precedes the light chain variable domain, connected by a suitable oligo- or polypeptide linker. Both LLH or HLL SCFv derivatives of the 98.6 and 447D MAbs may be constructed using a variety of oligo- and polypeptide linkers. In this example, the 98.6 LLH SCFv was joined at its C-terminus (residue 113 of the VH variable domain) to the N-terminus of the 447D LLH SCFv (residue 1 of the Vλ variable domain). Alternatively, the 447D LLH SCFv is joined at its C-terminus (residue 113 of the VH variable domain) to the N-terminus of the 98.6 LLH SCFv (residue 1 of the Vκ variable domain). Either LLH SCFv may be substituted for by the corresponding HLL SCFv, or modifications thereof. The two SCFv's were joined either directly, or via an oligo- or polypeptide linker. The C-terminus of the second SCFv was fused in turn to the hinge and Fc region (residues 226–477) of the human IgG2 heavy chain, followed by (from N- to C-terminus): the 18 residue human IgG3 M1 membrane hinge, the CD4 TM domain (residues 372–395 of the mature polypeptide), and the ζ CYT domain (residues 31–142 of the mature polypeptide). Mammalian transduction-expression vectors for the 98.6 SCFv/447D SCFv MSCRs described in this example were constructed using plasmid pRT43.2F16, a retroviral vector which directs the expression of the SAb-ζ monospecific chimeric receptor F16 (U.S. Pat. No. 5,359,046) which contains the 98.6 LLH SCFv domain fused to (from N- to C-terminus): the Fc domain of human IgG1 heavy chain, the IgG3 M1 membrane hinge domain, the CD4 TM domain, and the ζ CYT domain. Plasmid pRT43.2F16 was constructed from three fragments: 1) a 6.7 kb vector fragment obtained by digestion of pRT43.2F3 (as described in U.S. patent application Ser. No. 08/258,152) with EcoRI and Apa I, 2) a 1.4 kb fragment encoding the 98.6 LLH SCFv domain and the N-terminal portion of the IgG1 Fc domain, obtained by digestion of pIKF16 (U.S. Pat. No. 5,359,046) with EcoRI and NsiI, and 3) a 0.7 kb fragment encoding the remainder of the IgG1 Fc domain, the IgG3 membrane hinge domain, the CD4 TM domain and the ζ CYT domain, obtained by digestion of pIKF16 with NsiI and ApaI. The construction of MSCRs with an IgG2 Fc domain using a monospecific chimeric receptor with an IgG1 Fc domain was facilitated by the fact that the CH3 regions of the human IgG1 and IgG2 Fc domains share a unique NsiI site, and the amino acid sequences of each which follow this restriction site are identical. In each example, the correct expression plasmid was identified by restriction mapping.

Example 5A
SAb(αgp41)-SAb(αgp120)-Fc-ζ pRT-SAb(αgp41)-SAb(αgp120)-Fc-ζ directs the expression of a hybrid protein consisting of the Vκ signal sequence and SCFv domain of 98.6-LLH joined at its C-terminus (98.6-VH residue 113) to the N-terminus of the SCFv domain of 447D-LLH (447D-Vλ residue 1), followed by (from N- to C-terminus): the human IgG2 hinge and Fc domains (residues 226–478), the IgG3 Ml membrane hinge domain, the CD4 TM domain (residues 372–395 of the mature polypeptide) and the ζ CYT domain (residues 31–142 of the mature polypeptide). This plasmid is constructed from two fragments: 1) a 7.5 kb vector fragment encoding the C-terminal portion of the IgG1 Fc domain (identical to the corresponding IgG2 region), the IgG3 M1 domain, the CD4 TM domain and the ζ CYT domain, obtained by digestion of pIK43.2F16 with EcoRI and NsiI, and 2) a 2.0 kb fragment encoding the 98.6-LLH SCFv domain, the 447D-LLH SCFv domain and the N-terminal portion of the IgG2 Fc domain, obtained by digestion of pIK-SAb(αgp41)-SAb(αgp120)-Fc with EcoRI and NsiI.

Example 5B
SAb(αgp41)-L1-SAb(αgp120)-Fc-ζ pRT-SAb(αgp41)-L1-SAb(αgp120)-Fc-ζ directs the expression of a hybrid protein consisting of the Vκ signal sequence and SCFv domain of 98.6-LLH joined at its C-terminus (98.6-VH residue 113) by a 14 amino acid peptide linker (Gly-Ser-Thr-Ser-Gly-Ser-Gly-Lys-Ser-Ser-Glu-Gly-Lys-Gly) (SEQ ID NO:23) to the N-terminus of the SCFv domain of 447D-LLH (447D-Vλ residue 1), followed by (from N- to C-terminus): the human IgG2 hinge and Fc domains (residues 226–478), the IgG3 M1 membrane hinge domain, the CD4 TM domain (residues 372–395 of the mature polypeptide) and the ζ CYT domain (residues 31–142 of the mature polypeptide). This plasmid was constructed from two fragments: 1) a 7.5 kb vector fragment encoding the C-terminal portion of the IgG1 Fc domain (identical to the corresponding IgG2 region), the IgG3 M1 domain, the CD4 TM domain and the ζ CYT domain, obtained by digestion of pIK43.2F16 with EcoRI and NsiI, and 2) a 2.0 kb fragment encoding the 98.6-LLH SCFv domain, the 14 amino acid peptide linker, the 447D-LLH SCFv domain and the N-terminal portion of the IgG2 Fc domain, obtained by digestion of pIK-SAb(αgp41)-L1-SAb(αgp120)-Fc with EcoRI and NsiI.

Example 5C
SAb(αgp41)-L2-SAb(αgp120)-Fc-ζ pRT-SAb(αgp41)-L2-SAb(αgp120)-Fc-ζ directs the expression of a hybrid protein consisting of the Vκ signal sequence and SCFv domain of 98.6-LLH joined at its C-terminus (98.6-VH residue 113) by a 25 amino acid linker (Ser-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Gly) (SEQ ID NO:24) to the N-terminus of the SCFv domain of 447D-LLH (447D-Vλ residue 1), followed by (from N- to C-terminus): the human IgG2 hinge and Fc domains (residues 226–478), the IgG3 M1 membrane hinge domain, the CD4 TM domain (residues 372–395 of the mature polypeptide) and the λ CYT domain (residues 31–142 of the mature polypeptide). This plasmid was constructed from two fragments: 1) a 7.5 kb vector fragment encoding the C-terminal portion of the IgG1 Fc domain (identical to the corresponding IgG2 region), the IgG3 M1 domain, the CD4 TM domain and the ζ CYT domain, obtained by digestion of pIK43.2F16 with EcoRI and NsiI, and 2) a 2.1 kb fragment encoding the 98.6-LLH SCFv domain, the 25 amino acid peptide linker, the 447D-LLH SCFv domain and the N-terminal portion of the IgG2 Fc domain, obtained by digestion of pIK-SAb(αgp41)-L2-SAb(αgp120)-Fc with EcoRI and NsiI.

Example 5D
SAb(αgp41)-L3-SAb(αgp120)-Fc-ζ pRT-SAb(αgp41)-L3-SAb(αgp120)-Fc-ζ directs the expression of a hybrid protein consisting of the Vκ signal sequence and SCFv domain of 98.6-LLH joined at its C-terminus (98.6-VH residue 113) by a 10 amino acid linker (Asp-Lys-Thr-His-Thr-Ser-Pro-Pro-Ser-Pro) (SEQ ID NO:25) to the N-terminus of the SCFv domain of 447D-LLH (447D-Vλ residue 1), followed by (from N- to C-terminus): the human IgG2 hinge and Fc domains (residues 226–478), the IgG3 M1 membrane hinge domain, the CD4 TM domain (residues 372–395 of the mature polypeptide) and the ζ CYT domain (residues 31–142 of the mature polypeptide). This plasmid is constructed from two fragments: 1) a 7.5 kb vector fragment encoding the C-terminal portion of the IgG1 Fc domain (identical to the corresponding IgG2 region), the IgG3 M1 domain, the CD4 TM domain and the ζ CYT domain, obtained by digestion of pIK43.2F16 with EcoRI and NsiI, and 2) a 2.0 kb fragment encoding the 98.6-LLH SCFv domain, the 10 amino acid peptide linker, the 447D-LLH SCFv domain and the N-terminal portion of the IgG2 Fc domain, obtained by digestion of pIK-SAb(αgp41)-L3-SAb(αgp120)-Fc with EcoRI and NsiI.

Example 5E
SAb(αgp41)-L4-SAb(αgp120)-Fc-ζ pRT-SAb(αgp41)-L4-SAb(αgp120)-Fc-ζ directs the expression of a hybrid protein consisting of the Vκ signal sequence and SCFv domain of 98.6-LLH joined at its C-terminus (98.6-VH residue 113) by an 18 amino acid linker (Glu-Leu-Gln-Leu-Glu-Glu-Ser-Ser-Ala-Glu-Ala-Gln-Asp-Gly-Glu-Leu-Asp) (SEQ ID NO:26) to the N-terminus of the SCFv domain of 447D-LLH (447D-Vλ residue 1), followed by (from N- to C-terminus): the human IgG2 hinge and Fc domains (residues 226–478), the IgG3 M1 membrane hinge domain, the CD4 TM domain (residues 372–395 of the mature polypeptide) and the ζ CYT domain (residues 31–142 of the mature polypeptide). This plasmid is constructed from two fragments: 1) a 7.5 kb vector fragment encoding the C-terminal portion of the IgG1 Fc domain (identical to the corresponding IgG2 region), the IgG3 M1 domain, the CD4 TM domain and the ζ CYT domain, obtained by digestion of pIK43.2F16 with EcoRI and NsiI, and 2) a 2.0 kb fragment encoding the 98.6-LLH SCFv domain, the 18 amino acid peptide linker, the 447D-LLH SCFv domain and the N-terminal portion of the IgG2 Fc domain, obtained by digestion of pIK-SAb(αgp41)-L4-SAb(αgp120)-Fc with EcoRI and NsiI.

Example 6
MSCRs comprising an antibody extracellular clustering domain, a ligand-receptor (CD4) extracellular clustering domain, and a ζ family signaling domain.

Multispecific chimeric receptors (MSCRs) were created from multispecific antibodies which contain two or more extracellular clustering domains (ECDs), at least one of which is derived from an antibody and/or single-chain antibody, or modifications thereof, and at least one of which is derived from a ligand-receptor binding domain, or modifications thereof. The constructs described in this example contain the 447D LLH SCFv domain, and the human CD4 V1–V4 domains, which bind with high affinity to the HIV-1 gp120 envelope glycoprotein. Alternatively, the 447D SCFv's are created as HLL constructs in which the heavy chain variable domain precedes the light chain variable domain, connected by a suitable oligo- or polypeptide linker. Both LLH or HLL SCFv derivatives of the 447D MAb may be constructed using a variety of oligo- and polypeptide linkers. Portions of CD4 other than the entire CD4 EXT domain (residues 1–371 of the mature polypeptide) made be employed, including various truncations and/or modifications thereof. In this example, the 447D LLH SCFv was joined at its C-terminus (residue 113 of the VH variable domain) to the N-terminus of the CD4 protein (residue 1 of the mature polypeptide). Alternatively, the CD4 protein is joined at the C-terminus of its entire EXT domain (residue 371 of the mature polypeptide, or truncations thereof, e.g. residue 180 which resides at the C-terminus of the CD4 V1 & V2 domains) to the N-terminus of the 447 LLH SCFv (residue 1 of the Vλ variable domain). The 447D LLH SCFv may be substituted for by the corresponding HLL SCFv, or modifications thereof. The 447D LLH SCFv was joined to the CD4 protein either directly, or via an oligo- or polypeptide linker. The C-terminus of the CD4 EXT domain, was fused in turn to the CD4 TM domain (residues 372–395 of the mature polypeptide), and the ζ CYT domain (residues 31–142 of the mature polypeptide). Mammalian transduction-expression vectors for the 447D SCFv/CD4 MSCRs described in this example were constructed using pRT43.2F3, a retroviral vector which directs the expression of the CD4-ζ monospecific chimeric receptor F3 (U.S. Pat. No. 5,359,046) comprised of the CD4 EXT and TM domains fused to the ζ CYT domain. The construction of MSCRs with a C-terminal CD4 EXT domain was facilitated by using a unique NheI restriction site in CD4 which is present in both the 447D SCFv/CD4 multispecific antibody and the CD4ζ monospecific chimeric receptor. In each example, the correct expression plasmid was identified by restriction mapping.

Example 6A

SAb(αgp120)-CD4-ζ pRT-SAb(αgp120)-CD4ζ directs the expression of a hybrid protein consisting of the Vλ secretion leader and SCFv domain of 447D-LLH joined at its C-terminus (447D-VH residue 113) to the CD4 EXT and TM domains (residues 1–395 of the mature polypeptide) and the ζ CYT domain (residues 31–142 of the mature polypeptide). This plasmid is constructed from three fragments: 1) a 6.7 kb vector fragment obtained by digesting pRT43.2F3 with EcoRI and ApaI, 2) a 1.4 kb fragment encoding the 447D-LLH SCFv domain and the N-terminal portion of the CD4 EXT domain, obtained by digestion of pIKSAb(αgp120)-CD4-Fc with EcoRI and NheI, and 3) a 1.2 kb fragment encoding the C-terminal portion of the CD4 EXT domain, the CD4 TM domain and the ζ CYT domain, obtained by digestion of pIK43.2F3 with NheI and ApaI.

Example 6B

SAb(αgp120)-L1-CD4-ζ pRT-SAb(αgp120)-L1-CD4ζ directs the expression of a hybrid protein consisting of the Vλ secretion leader and SCFv domain of 447D-LLH joined at its C-terminus (447D-VH residue 113) by a 14 amino acid linker (Gly-Ser-Thr-Ser-Gly-Ser-Gly-Lys-Ser-Ser-Glu-Gly-Lys-Gly) (SEQ ID NO:23) to the CD4 EXT and TM domains (residues 1–395 of the mature polypeptide) and the ζ CYT domain (residues 31–142 of the mature polypeptide). This plasmid was constructed from three fragments: 1) a 6.7 kb vector fragment obtained by digesting pRT43.2F3 with EcoRI and ApaI, 2) a 1.5 kb fragment encoding the 447D-LLH SCFv domain, the 14 amino acid peptide linker and the N-terminal portion of the CD4 EXT domain, obtained by digestion of pIKSAb(αgp120)-L1-CD4-Fc with EcoRI and NheI, and 3) a 1.2 kb fragment encoding the C-terminal portion of the CD4 EXT domain, the CD4 TM domain and the ζ CYT domain, obtained by digestion of pIK43.2F3 with NheI and ApaI.

Example 6C

SAb(αgp120)-L2-CD4-ζ pRT-SAb(αgp120)-L2-CD4ζ directs the expression of a hybrid protein consisting of the Vλ secretion leader and SCFv domain of 447D-LLH joined at its C-terminus (447D-VH residue 113) by a 25 amino acid linker (Ser-Ser-Ala-Asp-Asp-Ala-Lys-Lys-Asp-Ala-Ala-Lys-Lys-Asp-Asp-Ala-Lys-Lys-Asp-Asp-Ala-Lys-Lys-Asp-Gly) (SEQ ID NO:24) to the CD4 EXT and TM domains (residues 1–395 of the mature polypeptide) and the ζ CYT domain (residues 31–142 of the mature polypeptide). This plasmid was constructed from three fragments: 1) a 6.7 kb vector fragment obtained by digesting pRT43.2F3 with EcoRI and ApaI, 2) a 1.5 kb fragment encoding the 447D-LLH SCFv domain, the 25 amino acid peptide linker and the N-terminal portion of the CD4 EXT domain, obtained by digestion of pIKSAb(αgp120)-L2-CD4-Fc with EcoRI and NheI, and 3) a 1.2 kb fragment encoding the C-terminal portion of the CD4 EXT domain, the CD4 TM domain and the ζ CYT domain, obtained by digestion of pIK43.2F3 with NheI and ApaI.

Example 6D

SAb(αgp120)-L3-CD4-ζ pRT-SAb(αgp120)-L3-CD4-ζ directs the expression of a hybrid protein consisting of the Vλ secretion leader and SCFv domain of 447D-LLH joined at its C-terminus (447D-VH residue 113) by a 10 amino acid linker (Asp-Lys-Thr-His-Thr-Ser-Pro-Pro-Ser-Pro) (SEQ ID NO:25) to the CD4 EXT and TM domains (residues 1–395 of the mature polypeptide) and the ζ CYT domain (residues 31–142 of the mature polypeptide). This plasmid is constructed from three fragments: 1) a 6.7 kb vector fragment obtained by digesting pRT43.2F3 with EcoRI and ApaI, 2) a 1.4 kb fragment encoding the 447D-LLH SCFv domain, the 10 amino acid peptide linker and the N-terminal portion of the CD4 EXT domain, obtained by digestion of pIKSAb(αgp120)-L3-CD4-Fc with EcoRI and NheI, and 3) a 1.2 kb fragment encoding the C-terminal portion of the CD4 EXT domain, the CD4 TM domain and the ζ CYT domain, obtained by digestion of pIK43.2F3 with NheI and ApaI.

Example 6E

SAb(αgp120)-L4-CD4-ζ pRT-SAb(αgp120)-L4-CD4-ζ directs the expression of a hybrid protein consisting of the Vλ secretion leader and SCFv domain of 447D-LLH joined at its C-terminus (447D-VH residue 113) by an 18 amino acid linker (Glu-Leu-Gln-Leu-Glu-Glu-Ser-Ser-Ala-Glu-Ala-Gln-Asp-Gly-Glu-Leu-Asp) (SEQ ID NO:26) to the CD4 EXT and TM domains (residues 1–395 of the mature polypeptide) and the ζ CYT domain (residues 31–142 of the mature polypeptide). This plasmid is constructed from three fragments: 1) a 6.7 kb vector fragment obtained by digesting pRT43.2F3 with EcoRI and ApaI, 2) a 1.5 kb fragment encoding the 447D-LLH SCFv domain, the 18 amino acid peptide linker and the N-terminal portion of the CD4 EXT domain, obtained by digestion of pIKSAb(αgp120)-L4-CD4-Fc with EcoRI and NheI, and 3) a 1.2 kb fragment encoding the C-terminal portion of the CD4 EXT domain, the CD4 TM domain and the ζ CYT domain, obtained by digestion of pIK43.2F3 with NheI and ApaI.

Example 7

Multispecific antibodies & MSCRs comprising two antibody extracellular clustering domains, a ligand-receptor (CD4) extracellular clustering domain, and a ζ family signaling domain.

Multispecific antibodies and MSCRs are created which contain three or more extracellular clustering domains (ECDs), at least one of which is derived from an antibody and/or single-chain antibody, or modifications thereof, and at least one of which is derived from a ligand-receptor binding domain, or modifications thereof. The constructs described in this example contain the 98.6 LLH SCFv domain, the 447D LLH SCFv domain, and the human CD4 V1–V2 domains, in the case of the multispecific antibodies, and the entire CD4 EXT domains, in the case of the MSCRs. Alternatively, the 98.6 and 447D SCFv's are created as HLL constructs in which the heavy chain variable domain precedes the light chain variable domain, connected by a suitable oligo- or polypeptide linker. Both LLH or HLL SCFv derivatives of the 98.6 and 447D MAb may be constructed using a variety of oligo- and polypeptide linkers and substituted accordingly in the multispecific antibodies and MSCRs herein described. Portions of CD4 other than the entire CD4 EXT or V1–V2 domains may similarly be employed, including various truncations and/or modifications thereof. In this example, the order of ECDs is (from N- to C-terminal): the 98.6 LLH SCFv domain, the 447D LLH SCFv domain, and the CD4 EXT domain. Alternatively, it is possible to create variants of all of the possible permutations of the order of these three as well as other domains. The 98.6 LLH SCFv, 447D LLH SCFv, CD4 and other ECDs may be linked either directly, or via various oligo- or polypeptide linkers. In the event that a SCFv is the most C-terminal ECD in an MSCR, it may be fused in turn to the hinge and Fc region (residues 226–477) of the human IgG2 heavy chain, followed by (from N- to C-terminus): the 18 residue human IgG3 M1 membrane hinge, the CD4 TM domain (residues 372–395 of the mature polypeptide), and the ζ CYT domain (residues 31–142 of the mature polypeptide). In the event that CD4 is the most C-terminus ECD of the MSCR, it may be fused in turn to the CD4 TM domain (residues 372–395 of the mature polypeptide), and the ζ CYT domain (residues 31–142 of the mature polypeptide). In each example, the correct expression plasmid was identified by restriction mapping.

Example 7A

SAb(αgp41)-(Lx)-SAb(αgp120)-(Ly)-CD4-Fc

A series of plasmids of the general structure pIKSAb (αgp41)-(Lx)-SAb(αgp120)-(Ly)-CD4-Fc, where Lx and Ly are any one of a number of various oligo- and polypeptide linkers including L1, L2, L3, L4 or no linker, direct the expression of a series of hybrid proteins consisting (from N- to C-terminus) of 1) the Vκ signal sequence and 98.6-LLH SCFv domain, 2) linker Lx, 3) the 447D-LLH SCFv, 4) linker Ly, 5) a portion of the CD4 EXT domain (residues 1–180 of the mature polypeptide), and 5) the human IgG2 hinge and Fc domains (residues 226–478). These plasmids are constructed from three fragments: 1) a 4.3 kb vector fragment obtained by digestion of pIK1.1 with EcoRI and BglII, 2) a 1.7 kb fragment encoding the C-terminus of the 447D-LLH SCFv domain, linker Ly, the CD4 V1 & V2 domains, and the IgG2 Fc domain, obtained by digestion of one of the pIKSAb(αgp120)-Ly-CD4-Fc series of plasmids with SpeI and BglII, and 3) a 1.2 kb fragment encoding the entire 98.6-LLH SCFv domain, linker Lx, and the N-terminus of the 447D-LLH SCFv domain, obtained by digestion of one of the pIKSAb(αgp41)-Lx-SAb(αgp120)-Fc series of plasmids with EcoRI and SpeI.

Example 7B

SAb(αgp41)-(Lx)-SAb(αgp120)-(Ly)-CD4-ζ

A series of plasmids of the general structure pIKSAb (αgp41)-(Lx)-SAb(αgp120)-(Ly)-CD4ζ, where Lx and Ly are any one of a number of various oligo- and polypeptide linkers including L1, L2, L3, L4 or no linker, direct the expression of a series of hybrid proteins consisting (from N- to C-terminus) of 1) the Vκ signal sequence and 98.6-LLH SCFv domain, 2) linker Lx, 3) the 447D-LLH SCFv, 4) linker Ly, 5) the CD4 EXT and TM domains (residues 1–395 of the mature polypeptide), and 5) the ζ CYT domain (residues 31–142 of the mature polypeptide). These plasmids are constructed from three fragments: 1) a 6.7 kb vector fragment obtained by digesting pRT43.2F3 with EcoRI and ApaI, 2) a 2.2 kb fragment encoding the the entire 98.6-LLH SCFv domain, linker Lx, the entire 447D-LLH SCFv domain, linker Ly, and the N-terminal portion of the CD4 EXT domain, obtained by digestion of pIK-SAb (αgp41)-Lx-SAb(αgp120)-Ly-CD4-Fc with EcoRI and NheI, and 3) a 1.2 kb fragment encoding the C-terminal portion of the CD4 EXT domain, the CD4 TM domain and the ζ CYT domain, obtained by digestion of pIK43.2F3 with NheI and ApaI.

Example 8

Expression & characterization of MSCRs

To determine whether each MSCR polypeptide can be efficiently expressed and transported to the cell surface, and thus properly folded, a corresponding mammalian transduction-expression vector is used to transfect human 293 embryonic kidney cell line. Following transfection, the expression of each construct is evaluated by radioimmunoprecipitation, and its transport to the cell surface is evaluated by fluorescent-activated cell sorting (FACS) analysis.

Example 8A

Transfection of human 293 cells with NSCR expression vectors

For transfection, 293 cells were grown in DMEM:F12 media (JRH Biosciences) containing 10% fetal calf serum, and passaged at a 110 split ratio every 3 days. Twenty-four hours prior to transfection, 293 cells were plated at $5 \times 10^5$ cells per 10 cm culture dish. Ten μg of each expression plasmid DNA is transfected onto a 10 cm dish by the calcium phosphate coprecipitation method (Wigler et al. (1979) Cell 16:777). Twenty-four hours after transfection, the transfected cells were fed with fresh complete DMEM media. The expression of MSCR polypeptides was evaluated by FACS analysis and radioimmunoprecipitation analysis at 48 hours post-transfection.

Example 8B

FACS analysis of MSCR expression on 293 cells

Transfected 293 cells are rinsed once with PBS and incubated in PBS containing 10 mM EDTA for 5 minutes at room temperature. Cells are collected from plates, centrifuged and resuspended in PBS containing 1% fetal calf serum. Approximately $1 \times 10^6$ cells/sample are stained directly with saturating concentrations of FITC-conjugated mouse anti-human IgG or mouse anti-CD4 MAbs (Becton Dickinson Immunocytometry Systems, San Jose, Calif.). Mouse FITC-IgG1 and PE-IgG2a are used as negative control MAbs. All FACS analyses are performed in a FACStation (Becton Dickinson) as previously described (Weiss and Stobo, (1984) *J. Exp. Med.,* 160:1284–1299).

Example 8C

Radioimmunoprecipitation of MSCRs expressed in 293 cells

Transfected 293 cells are rinsed once with RPMI medium lacking methionine. Cells are cultured for additional 8 hours in 2 M1 of methionine-deficient RPMI supplemented with 200 μCi [35S]-methionine (1160 C/mmol, ICN Biomedicals, Inc., Irvine, Calif.). The labelled cells are lysed in RIPA buffer, and the cell lysates are incubated at 4° C. for 1 hour with either no antibody (Class 1 MSCRs contain the IgG2 Fc domain and bind Protein A directly) or mouse anti-CD4 OKT4A MAb (Ortho Diagnostic Systems, Raritan, N.J.). Ten microliters of Pansorbin is added to the lysates to precipitate the MSCR. Immunoprecipitates are washed three times in RIPA buffer, boiled in SDS sample buffer and analyzed by 10% SDS-polyacrylamide gel electrophoresis (SDS-PAGE). Gels are fixed in 20% methanol/10% acetic acid, then soaked in Enlightning solution for 15 min, dried and subjected to autoradiography. SDS-PAGE analysis reveals the molecular mass of MSCRs expressed in 293 cells.

Example 9
Biochemical and biological properties of human CD8+ T cells expressing MSCRs

Example 9A
Infection of human CD8+ T cells with MSCR-expressing retroviral vectors Human CD8+ T lymphocytes are isolated from peripheral blood lymphocytes (PBL) obtained from healthy donors by purification with the CEPRATE LC system (CellPro, Inc., Bothell, Wash.), followed by negative selection against CD4 cells using a T-25 MicroCELLector (AIS, Inc., Santa Clara, Calif.). Immediately after purification, cells are stimulated for 24 hours with an equal number of y-irradiated autologous PBMCs in AIM-V media (GibcoBRL, Grand Island, N.Y.) containing 10 ng/ml of OKT3 MAb and 100 units of human IL-2 (Chiron Corp., Emeryville, Calif.). Cells are then washed free of OKT3 and cultured in AR media (50% AIM-V, 50% RPMI, 4 mM Glutamine, 20 mM Hepes, 1 mM Na-Pyruvate, non-essential amino acids, and 100 units human IL-2) supplemented with 5% heat inactivated human AB plasma (Sigma, St. Louis, Mo.). Retrovirus is prepared in the TIN-4 cell line derived from thymidine kinase-expressing human 293 cells. For the transduction of human CD8+ +cells, TIN-4 cells are seeded at $5\times10^5$ cell/plate in 6-well plates (Corning Glass, Corning, N.Y.) in complete DMEM medium 48 hours prior to transfection. Ten micrograms of MSCEFR construct in the retroviral vector pRT43.2 (as described in U.S. patent application Ser. No. 08/258,152) are transfected per plate in the absence or presence of packaging plasmids by the calcium phosphate coprecipitation method. Following transfection, 1.5 M1 of fresh AR medium containing 100 units/ml of human IL-2 is added to each well of the plate. Three hours later, $5\times10^5$ of CD8+ T cells in AR media containing 100 units/ml of human IL-2 and 2 µg/ml of polybrene are added to each well of the plate. CD8+ T cells are removed from the 6-well plates 24 hours later and then transduced a second time by the same procedure. Newly transduced CD8+ T cells are maintained in AR media.

Example 9B
FACS analysis of MSCR expression in human CD8+ T cells

At various times following transduction, CD8+ T cells are harvested and washed with PBS containing 1% FCS. Approximately $1\times10^6$ CD8+ T cells are stained with specific antibodies for FACS analysis as described in Example 8B.

Example 9C
Immunprecipitation analysis of MSCR expression in human CD8+ T cells At various times following transduction, human CD8+ T cells are harvested and placed in methionine-depleted AR media supplemented with 200 µCi [35S]-methionine (1160 Ci/mmol, ICN Biomedicals, Inc.). Cells are lysed in RIPA buffer and then incubated at 4° C. for 1 hour with either with no antibody (Fc-containing MSCRs) or mouse anti-CD4 OKT4A MAb (CD4-containing MSCRs). Ten microliters of Pansorbin are then added to the lysates to precipitate the MSCR polypeptide. The immunoprecipitates are washed three times in RIPA buffer, boiled in SDS sample buffer and analyzed by 8% SDS-polyacrylamide gel electrophoresis. Gels are fixed in 20% methanol/10% acetic acid, then soaked in Enlightning solution for 15 minutes, dried and subjected to autoradiography. SDS-PAGE analysis reveals the molecular mass of MSCRs expressed in human CD8+ T cells.

Example 9D
Cytolytic activity of MSCR-expressing human CD8+ T cells

To determine the cytolytic activity of MSCR-expressing human CD8+ T cells, in vitro cytolytic assays are carried out with target cells expressing wild-type and mutant HIV-1 antigens. HIV-1 infected human T cells or gp160-expressing 293 cells are compared with uninfected human T cells or untransfected 293 cells for their ability to be cytolytic targets for MSCR-expressing CD8+ T cells. Plasmids pIKenv+/rev+/tat−, pIKenvG370R/rev+/tat− and pIKenvR315Q/rev+/tat− are used to generate stably transfected 293 cells as described in U.S. Pat. No. 5,359,046, which express wild-type or mutant env proteins. These gp160-expressing 293 cells or HIV-1 infected human T cells are labeled at 37° C. for 18 hours with [$^3$H]TdR (Roberts et al, *Blood* 84:2878–2889 (1994)), washed and aliquoted to 96-well V-bottom plates at $\times10^4$/well. Serial dilutions of MSCR-expressing human CD8+ T cells are made up to achieve an effector to target (E:T) ratio ranging from 100:1 to 0.1:1. Samples are set up in triplicate and incubations are carried out for 6 hours at 37° C. Following incubation, aliquots of the culture supernatant are removed and counted in a liquid scintillation counter. Spontaneous release (SR) is obtained in a negative control sample lacking MSCR-expressing human CD8+ T cells; maximum release (MR) is obtained from a positive control sample by lysing target cells with 1N HCl. The percent specific lysis is calculated from the following equation:

$$\% \text{ specific lysis} = (SR_{cpm} - \text{Sample}_{cpm})/(\text{Sample}_{cpm} - MR_{cpm}) \times 100\%.$$

The cytolytic activity of CD8+ T cells expressing various MSCRs and monospecific chimeric receptors as effector cells on target cells infected with various HIV-1 isolates or target cells transfected with wild-type or mutant env genes are compared. In particular, MSCRs which direct the efficient cytolysis of a range of primary HIV-1 isolates are considered good candidates for therapeutic application.

All publications, patents, and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

---

What is claimed is:

1. A DNA molecule encoding a chimeric membrane bound protein, said protein comprising in the N-terminal to C-terminal direction:
   at least two extracellular inducer-responsive clustering domains in tandem to form a multispecific extracellular inducer-responsive clustering domain that binds specifically to at least one inducer molecule which results in the dimerization or oligomerization of said multispecific extracellular domain;
   a transmembrane domain; and
   a cytoplasmic signaling domain comprising a ζ or η chain of the T-cell receptor, or a Janus kinase,
   wherein when said membrane bound protein is expressed in a selected host cell under conditions suitable for expression, said membrane bound protein initiates a signal in said host cell on binding to said at least one inducer molecule.

2. The DNA molecule according to claim 1 wherein at least one said extracellular inducer responsive clustering domain is an antibody or single-chain antibody or portions or modifications thereof containing inducer binding and clustering activity.

3. The DNA molecule according to claim 2 wherein at least one said extracellular inducer responsive clustering domain is a cell differentiation antigen.

4. The DNA molecule according to claim 1 wherein at least one said extracellular inducer-responsive clustering domain is CD4 and at least another said extracellular inducer-responsive clustering domain is an antibody or single chain antibody.

5. The DNA molecule according to claim 2 wherein at least one said antibody or single chain antibody recognizes an antigen from a virus selected from the group consisting of HIV, hepatitis A, B and C viruses, Kaposi's sarcoma associated Herpes virus, Herpes Simplex viruses, Herpes Zoster virus, cytomegalovirus, papilloma virus, respiratory syncytial virus and influenza virus.

6. The DNA molecule according to claim 2 wherein at least one said antibody or said single chain antibody recognizes an antigen on a cancer cell selected from the group consisting of interleukin 14 receptor, CD19, CD20, Lewis Y antigen, CEA, Tag72 antigen, EGF-R and HER-2.

7. The DNA molecule according to claim 1 wherein said transmembrane domain is naturally associated with one of said extracellular inducer responsive clustering domains.

8. The DNA molecule according to claim 1 wherein said transmembrane domain is naturally associated with said signaling domain.

9. A DNA molecule encoding a chimeric membrane bound protein, said chimeric protein comprising in the N-terminal to C-terminal direction:
   at least two extracellular inducer-responsive clustering domains in tandem to form a multispecific extracellular inducer-responsive clustering domain that binds specifically to at least one inducer molecule which results in the dimerization or oligomerization of said multispecific extracellular domain;
   a transmembrane domain;
   a cytoplasmic domain comprising a Janus kinase; and
   a cytoplasmic domain comprising ζ or η chain of the T-cell receptor;
   wherein when said membrane bound protein is expressed in a selected host cell under conditions suitable for expression, said membrane bound protein initiates a signal for proliferation and effector function in said host cell on binding to said at least one inducer molecule.

10. A DNA molecule encoding a chimeric membrane bound protein, said chimeric protein comprising in the N-terminal to C-terminal direction:
    at least two extracellular inducer-responsive clustering domains in tandem to form a multispecific extracellular inducer-responsive clustering domain that binds specifically to at least one inducer molecule which results in the dimerization or oligomerization of said multispecific extracellular domain;
    a transmembrane domain;
    a cytoplasmic domain comprising ζ or η chain of the T-cell receptor; and
    a cytoplasmic domain comprising a Janus kinase;
    wherein when said membrane bound protein is expressed in a selected host cell under conditions suitable for expression, said membrane bound protein initiates a signal for proliferation and effector function in said host cell on binding to said at least one inducer molecule.

11. The DNA molecule according to claim 9 or 10, wherein at least one said extracellular inducer responsive clustering domain is an antibody or single-chain antibody or portions or modifications thereof containing inducer binding and clustering activity.

12. The DNA molecule according to claim 9 or 10, wherein at least one said extracellular inducer responsive clustering domain is a cell differentiation antigen.

13. The DNA molecule according to claim 9 or 10, wherein at least one said extracellular inducer-responsive clustering domain is CD4 and at least one other said extracellular inducer-responsive clustering domain is a single chain antibody.

14. The DNA molecule according to claim 11, wherein at least one said single chain antibody recognizes an antigen from a virus selected from the group consisting of HIV, hepatitis A, B and C viruses, Kaposi's sarcoma associated Herpes virus, Herpes Simplex viruses, Herpes Zoster virus, cytomegalovirus, respiratory syncytial virus, influenza virus and papilloma virus.

15. The DNA molecule according to claim 9, wherein at least one said single chain antibody recognizes an antigen on a cancer cell selected from the group consisting of interleukin 14 receptor, CD19, CD20, Lewis Y antigen, CEA, Tag72 antigen, EGF-R and HER-2.

16. The DNA molecule according to claim 10, wherein said transmembrane domain is naturally associated with one of said multispecific extracellular inducer-responsive clustering domains, or ζ or η chain of the T-cell receptor.

17. The DNA molecule according to claim 9, wherein said transmembrane domain is naturally associated with one of said multispecific extracellular inducer-responsive clustering domains.

18. A DNA molecule encoding a hybrid extracellular and intracellular multispecific chimeric receptor protein, said chimeric protein comprising in the N-terminal to C-terminal direction:
at least two extracellular inducer-responsive clustering domains in tandem to form a multispecific extracellular inducer-responsive clustering domain that binds specifically to at least one inducer molecule which results in the dimerization or oligomerization of said multispecific extracellular domain;
a transmembrane domain:
a cytoplasmic domain comprising a Janus kinase; and
an intracellular inducer-responsive clustering domain comprising an immunophilin or a cyclophilin;
wherein when said chimeric receptor protein is expressed in a selected host cell under conditions suitable for expression, said receptor protein initiates a signal for proliferation in said host cell on binding to said at least one inducer molecule.

19. The DNA of claim 18, wherein at least one said extracellular clustering domains is an antibody or single-chain antibody or portions or modifications thereof containing inducer binding and clustering antibody.

20. The DNA of claim 18, wherein at least one said extracellular clustering domains is a cell differentiation antigen.

21. A DNA molecule encoding a hybrid multispecific chimeric receptor protein, said protein comprising in the N-terminal to C-terminal direction:
at least two extracellular inducer-responsive clustering domains in tandem to form a multispecific extracellular inducer-responsive clustering domain that binds specifically to at least one inducer molecule which results in the dimerization or oligomerization of said multispecific extracellular domain;
a transmembrane domain;
a cytoplasmic domain comprising a Janus kinase;
a cytoplasmic domain comprising a ζ or η chain of the T-cell receptor; and
an intracellular inducer-responsive clustering domain comprising an immunophilin or a cyclophilin;
wherein when said hybrid multispecific chimeric receptor is expressed in a selected host cell under conditions suitable for expression, said receptor protein initiates a signal for proliferation and effector function in said host cell on binding to said at least one inducer molecule.

22. The DNA of claim 21, wherein at least one said extracellular clustering domains is an antibody or single-chain antibody or portions or modifications thereof containing inducer binding and clustering activity.

23. The DNA of claim 21, wherein at least one said extracellular clustering domains is a cell differentiation antigen.

24. The DNA molecule according to claim 18 or 21, wherein said intracellular inducer responsive clustering domain binds to a natural or synthetic inducer that is cell membrane permeable and induces the clustering of said intracellular inducer responsive domain.

25. An expression cassette comprising a transcriptional initiation region, a DNA molecule according to claim 1 under the transcriptional control of said transcriptional initiation region and a transcriptional termination region.

26. An expression cassette comprising a transcriptional initiation region, a DNA molecule according to claim 9 under the transcriptional control of said transcriptional initiation region and a transcriptional termination region.

27. An expression cassette comprising a transcriptional initiation region, a DNA molecule according to claim 10 under the transcriptional control of said transcriptional initiation region and a transcriptional termination region.

28. An expression cassette comprising a transcriptional initiation region, a DNA molecule according to claim 18 under the transcriptional control of said transcriptional initiation region and a transcriptional termination region.

29. An expression cassette comprising a transcriptional initiation region, a DNA molecule according to claim 21 under the transcriptional control of said transcriptional initiation region and a transcriptional termination region.

30. The expression cassette according to claim 25, 26, 27, 28 or 29 wherein said transcriptional initiation region is functional in a mammalian host.

31. A cell comprising a DNA molecule according to claim 1.

32. A cell comprising a DNA molecule according to claim 9.

33. A cell comprising a DNA molecule according to claim 10.

34. A cell comprising a DNA molecule according to claim 18.

35. A cell comprising a DNA molecule according to claim 21.

36. A cell comprising an DNA molecule that encodes a chimeric effector function receptor comprising an extracellular inducer-responsive clustering domain, a transmembrane domain, and a effector function signaling domain and further comprising a second DNA molecule according to claim 1.

37. A cell comprising a DNA molecule that encodes a chimeric effector function receptor comprising an extracellular inducer-responsive clustering domain, a transmembrane domain, and a effector function signaling domain, and further comprising a second DNA molecule according to claim 9.

38. The cell comprising a DNA molecule that encodes a chimeric receptor comprising an extracellular inducer-responsive clustering domain, a transmembrane domain, a transmembrane domain and an effector function signaling domain, and a second DNA molecule according to claim 10.

39. A cell comprising a DNA molecule that encodes a chimeric effector function receptor comprising an extracellular inducer-responsive clustering domain, a transmembrane domain, and an effector function signaling domain, and further comprising a second DNA molecule according to claim 18.

40. The cell comprising a DNA molecule that encodes a chimeric receptor comprising an extracellular inducer-responsive clustering domain, a transmembrane domain, a transmembrane domain and an effector function signaling domain, and a second DNA molecule according to claim 21.

41. The cell according to claim 31, 32, 33, 34, 35, 36, 37 or 39, wherein said cell is a mammalian cell.

42. The cell according to claim 31, 32, 33, 34, 35, 36, 37 or 39, wherein said cell is a human cell.

43. A chimeric protein comprising in the N-terminal to C-terminal direction:
   a multispecific extracellular inducer-responsive clustering domain comprising at least two domains in tandem that bind specifically to at least one inducer-molecule which results in the dimerization or oligomerization of said multispecific extracellular domain;
   a transmembrane domain; and
   a cytoplasmic domain comprising a $\zeta$ or $\eta$ chain of the T-cell receptor, or a Janus kinase;
   wherein when said chimeric protein is expressed as a membrane bound protein in a selected host cell under conditions suitable for expression, said membrane bound protein initiates a signal in said host cell on binding to said at least one inducer molecule.

44. A chimeric protein comprising in the N-terminal to C-terminal direction:
   a multispecific extracellular inducer-responsive clustering domain comprising at least two domains in tandem that bind specifically to at least one inducer-molecule which results in the dimerization or oligomerization of said multispecific extracellular domain;
   a transmembrane domain;
   a cytoplasmic domain comprising a Janus kinase; and
   a cytoplasmic domain comprising $\zeta$ or $\eta$;
   wherein when said chimeric protein is expressed as a membrane bound protein in a selected host cell under conditions suitable for expression, said membrane bound protein initiates a signal for proliferation and effector function in said host cell on binding to said at least one inducer molecule.

45. A chimeric protein comprising in the N-terminal to C-terminal direction:
   a multispecific extracellular inducer-responsive clustering domain comprising at least two domains in tandem that bind specifically to at least one inducer-molecule which results in the dimerization or oligomerization of said multispecific extracellular domain;
   a transmembrane domain;
   a cytoplasmic domain comprising $\zeta$ or $\eta$ chain of the T-cell receptor; and
   a cytoplasmic domain comprising a Janus kinase;
   wherein when said chimeric protein is expressed as a membrane bound protein in a selected host cell under conditions suitable for expression, said membrane bound protein initiates a signal for proliferation and effector function in said host cell on binding to said at least one inducer molecule.

46. A chimeric hybrid binding protein comprising in the N-terminal to C-terminal direction:
   a multispecific extracellular inducer-responsive clustering domain comprising at least two domains in tandem that bind specifically to at least one inducer molecule which results in the dimerization or oligomerization of said multispecific extracellular domain;
   a transmembrane domain;
   a cytoplasmic domain comprising a Janus kinase; and
   an intracellular inducer-responsive clustering domain comprising an immunophilin or a cyclophilin;
   wherein when said chimeric hybrid binding protein is expressed as a protein receptor in a selected host cell under conditions suitable for expression, said protein receptor initiates a signal for proliferation in said host cell on binding to either said inducer molecule or combinations thereof.

47. A chimeric hybrid binding protein comprising in the N-terminal to C-terminal direction:
   a multispecific extracellular inducer-responsive clustering domain comprising at least two domains in tandem that bind specifically to at least one inducer molecule which results in the dimerization or oligomerization of said multispecific extracellular domain;
   a transmembrane domain;
   a cytoplasmic domain comprising a Janus kinase;
   a cytoplasmic domain comprising $\zeta$ or $\eta$ chain of the T-cell receptor; and
   an intracellular inducer-responsive clustering domain comprising an immunophilin or a cyclophilin;
   wherein when said chimeric hybrid binding protein is expressed as a protein receptor in a selected host cell under conditions suitable for expression, said protein receptor initiates a signal for proliferation in said host cell on binding to either said inducer molecule or combinations thereof.

* * * * *

SEQUENCE LISTING (1) GENERAL INFORMATION:

(iii) NUMBER OF SEQUENCES: 26

```
(2) INFORMATION FOR SEQ ID NO:1:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

CTGCGTCAAC ACAGACTGTG AGGAGACGGT GACCAG                          36

(2) INFORMATION FOR SEQ ID NO:2:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

ACAGACTGTG AGGAGA                                                16

(2) INFORMATION FOR SEQ ID NO:3:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CTGCGTCAAC ACAGACTGAC CCTTACCCTC AGAAGATTTA CCCGACCCCG AGGTCGACCC     60

TGAGGAGACG GTGACCAG                                                  78

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AGAAGATTTA CCCGAC                                                16

(2) INFORMATION FOR SEQ ID NO:5:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CTGCGTCAAC ACAGACTGAC CGTCCTTCTT AGCGTCGTCC TTCTTAGCGT CGTCCTTCTT     60

AGCAGCGTCC TTCTTAGCGT CGTCAGCGGA AGATGAGGAG ACGGTGACCA G            111
```

```
(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCGTCGTCCT TCTTAG                                                     16

(2) INFORMATION FOR SEQ ID NO:7:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CTGCGTCAAC ACAGACTGTG GGACGGTGG GGATGTGTGA GTTTTGTCTG AGGAGACGGT      60

GACCAG                                                                66

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CGGTGGGGAT GTGTGA                                                     16

(2) INFORMATION FOR SEQ ID NO:9:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CTGCGTCAAC ACAGACTGGT CCAGCTCCCC GTCCTGCGCT TCGGCGCTCG ATTCTTCCAG     60

TTGCAGCTCT GAGGAGACGG TGACCAG                                         87

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TCGGCGCTCG ATTCTT                                                     16
```

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GCCCAGCACC ACTTTCTTTG AGCTCACGGT GACCGT                        36

(2) INFORMATION FOR SEQ ID NO:12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

ACTTTCTTTG AGCTCA                                          16

(2) INFORMATION FOR SEQ ID NO:13:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCCCAGCACC ACTTTCTTAC CCTTACCCTC AGAAGATTTA CCCGACCCCG AGGTCGACCC      60

TGAGCTCACG GTGACCGT                                        78

(2) INFORMATION FOR SEQ ID NO:14:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GCCCAGCACC ACTTTCTTAC CGTCCTTCTT AGCGTCGTCC TTCTTAGCGT CGTCCTTCTT      60

AGCAGCGTCC TTCTTAGCGT CGTCAGCGGA AGATGAGCTC ACGGTGACCG T             111

(2) INFORMATION FOR SEQ ID NO:15:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GCCCAGCACC ACTTTCTTTG GGGACGGTGG GGATGTGTGA GTTTTGTCTG AGCTCACGGT      60

GACCGT                                                                       66

(2) INFORMATION FOR SEQ ID NO:16:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
GCCCAGCACC ACTTTCTTGT CCAGCTCCCC GTCCTGCGCT TCGGCGCTCG ATTCTTCCAG      60

TTGCAGCTCT GAGCTCACGG TGACCGT                                         87
```

(2) INFORMATION FOR SEQ ID NO:17:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
TAGTCTAGGA TCTACTGGCT GCAGTTCTTG CTCTCCTCTG TC                        42
```

(2) INFORMATION FOR SEQ ID NO:18:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
ACTGGCTGCA GTTCTT                                                     16
```

(2) INFORMATION FOR SEQ ID NO:19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
AAAACTGTGC GTTACAATTC GTGGGTCCCC TCCTGAGGA                            39
```

(2) INFORMATION FOR SEQ ID NO:20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
TACAATTCGT GGGTCC                                                     16
```

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TCCTATTGTA ACAAATGCTT GCCCTGGTCC TCTCTGGAT                                   39

(2) INFORMATION FOR SEQ ID NO:22:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

AAATGCTTGC CCTGGT                                                            16

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Gly Ser Thr Ser Gly Ser Gly Lys Ser Ser Glu Gly Lys Gly
1               5                   10

(2) INFORMATION FOR SEQ ID NO:24:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Ser Ser Ala Asp Asp Ala Lys Lys Asp Ala Ala Lys Lys Asp Ala
1               5                   10                  15
Lys Lys Asp Asp Ala Lys Lys Asp Gly
            20                  25

(2) INFORMATION FOR SEQ ID NO:25:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Asp Lys Thr His Thr Ser Pro Pro Ser Pro
1               5                   10

```
(2) INFORMATION FOR SEQ ID NO:26:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Glu Leu Gln Leu Glu Glu Ser Ser Ala Glu Ala Gln Asp Gly Glu Leu
1               5                   10                  15

Asp
```